US011078303B2

(12) United States Patent
Akizumi et al.

(10) Patent No.: US 11,078,303 B2
(45) Date of Patent: *Aug. 3, 2021

(54) CURABLE COMPOSITION

(71) Applicant: TOKUYAMA DENTAL CORPORATION, Tokyo (JP)

(72) Inventors: Hironobu Akizumi, Tokyo (JP); Takuma Matsuo, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/465,018

(22) PCT Filed: Nov. 28, 2017

(86) PCT No.: PCT/JP2017/042522
§ 371 (c)(1),
(2) Date: May 29, 2019

(87) PCT Pub. No.: WO2018/101236
PCT Pub. Date: Jun. 7, 2018

(65) Prior Publication Data
US 2019/0292278 A1 Sep. 26, 2019

(30) Foreign Application Priority Data
Dec. 1, 2016 (JP) .............................. JP2016-234279

(51) Int. Cl.
A61K 6/083 (2006.01)
C08F 2/48 (2006.01)
C08K 3/11 (2018.01)
C08F 2/44 (2006.01)
C08F 20/18 (2006.01)
C08K 7/18 (2006.01)
A61K 6/16 (2020.01)
A61K 6/17 (2020.01)
A61K 6/62 (2020.01)
A61K 6/71 (2020.01)
A61K 6/76 (2020.01)
A61K 6/884 (2020.01)
A61K 6/887 (2020.01)

(52) U.S. Cl.
CPC ................. C08F 2/48 (2013.01); A61K 6/16 (2020.01); A61K 6/17 (2020.01); A61K 6/62 (2020.01); A61K 6/71 (2020.01); A61K 6/76 (2020.01); A61K 6/884 (2020.01); A61K 6/887 (2020.01); C08F 2/44 (2013.01); C08F 20/18 (2013.01); C08K 3/11 (2018.01); C08K 7/18 (2013.01); C08K 2201/005 (2013.01)

(58) Field of Classification Search
CPC ........................................................ A61K 6/17
See application file for complete search history.

(56) References Cited

U.S. PATENT DOCUMENTS

| 3,729,313 | A | 4/1973 | Smith |
| 3,741,769 | A | 6/1973 | Smith |
| 4,020,557 | A | 5/1977 | Rockett et al. |
| 5,545,676 | A | 8/1996 | Palazzotto et al. |
| 2004/0180983 | A1 | 9/2004 | Hara et al. |
| 2008/0319104 | A1 | 12/2008 | Klapdohr et al. |
| 2011/0196062 | A1 | 8/2011 | Craig |
| 2013/0096226 | A1* | 4/2013 | Toriyabe ............. A61K 6/887 523/115 |
| 2013/0172441 | A1 | 7/2013 | Takahata et al. |
| 2014/0206792 | A1 | 7/2014 | Ishizaka et al. |

(Continued)

FOREIGN PATENT DOCUMENTS

| EP | 1236459 A1 | 9/2002 |
| EP | 2583660 A1 | 4/2013 |

(Continued)

OTHER PUBLICATIONS

Extended European Search Report issued in corresponding European Application No. 17876044.3; dated Oct. 25, 2019 (13 pages).
Matsumura et al., "Adhesion Yearbook 2006," 1st Edition, Quintessence Publishing Co., Ltd., published Aug. 2006, pp. 129-137 (14 pages) with partial translation.
H. Miyazaki, "Science & Technique of Composite Resin Restoration," 1st Edition, Quintessence Publishing Co., Ltd., published Jan. 2010, pp. 48-49 (6 pages) with partial translation.
International Search Report issued in corresponding Japanese Application No. PCT/JP2017/042522; dated Jan. 23, 2018 (3 pages).
Written Opinion of the International Searching Authority issued in corresponding Japanese Application No. PCT/JP2017/042522; dated Jan. 23, 2018 (4 pages).
Office Action issued in corresponding Brazilian Application No. BR112019009456-3, dated Jul. 1, 2020 (47 pages).

(Continued)

Primary Examiner — Michael F Pepitone
(74) Attorney, Agent, or Firm — Osha Bergman Watanabe & Burton LLP

(57) ABSTRACT

Provided is a curable composition containing a polymerizable monomer (A), an organic-inorganic composite filler (B), and a polymerization initiator (C), wherein the organic-inorganic composite filler (B) includes an organic resin matrix (b1) and a spherical inorganic filler (b2) having an average primary particle size of 230-1000 nm, 90% or more of the number of individual particles constituting the spherical inorganic filler (b2) are present in a range of 5% greater or less than the average primary particle size, and the curable composition satisfies the following formulas (1) and (2):

$$nP < nF_{b2} \quad \text{(formula 1)}$$

$$\text{and } nM_{b1} < nF_{b2} \quad \text{(formula 2)}$$

In the formulas, nP represents the refractive index of the polymer of the polymerizable monomer (A) at 25° C., $nF_{b2}$ represents the refractive index of the spherical inorganic filler (b2) at 25° C., and $nM_{b1}$ represents the refractive index of the organic resin matrix (b1) at 25° C.

13 Claims, No Drawings

(56) References Cited

U.S. PATENT DOCUMENTS

| | | | |
|---|---|---|---|
| 2014/0213687 A1 | 7/2014 | Yamazaki et al. | |
| 2014/0295376 A1 | 10/2014 | Uchida et al. | |
| 2015/0094396 A1 | 4/2015 | Nakatsuka et al. | |
| 2015/0272833 A1 | 10/2015 | Toriyabe et al. | |
| 2017/0049665 A1 | 2/2017 | Kita et al. | |
| 2017/0196667 A1* | 7/2017 | Teramae | A61C 13/09 |
| 2018/0303721 A1 | 10/2018 | Akizumi et al. | |
| 2019/0192386 A1 | 6/2019 | Fukudome et al. | |

FOREIGN PATENT DOCUMENTS

| | | |
|---|---|---|
| EP | 2902007 A1 | 8/2015 |
| EP | 3366269 A1 | 8/2018 |
| EP | 3536302 A1 | 9/2019 |
| JP | S62-086003 A | 4/1987 |
| JP | S63-218703 A | 9/1988 |
| JP | S63-273602 A | 11/1988 |
| JP | 2001239661 A | 9/2001 |
| JP | 2004276492 A | 10/2004 |
| JP | 2005-089729 A | 4/2005 |
| JP | 2006117543 A | 5/2006 |
| JP | 2007-532518 A | 11/2007 |
| JP | 2012-505823 A | 3/2012 |
| JP | 2012-087086 A | 5/2012 |
| JP | 2012153640 A | 8/2012 |
| JP | 2014-189503 A | 10/2014 |
| JP | 2015-067594 A | 4/2015 |
| JP | 2016-169180 A | 9/2016 |
| RU | 2472708 C2 | 1/2013 |
| WO | 2009/014031 A1 | 1/2009 |
| WO | 2011158742 A1 | 12/2011 |
| WO | 2012/042911 A1 | 4/2012 |
| WO | 2012/176877 A1 | 12/2012 |
| WO | 2013/039169 A1 | 3/2013 |
| WO | 2014050634 A1 | 4/2014 |
| WO | 2015125470 A1 | 8/2015 |
| WO | 2017/069274 A1 | 4/2017 |
| WO | 2018/043595 A1 | 3/2018 |
| WO | 2018/101236 A1 | 6/2018 |

OTHER PUBLICATIONS

H. Shinoda et al., "Shikisai Kogaku Nyumon", Morikita Publishing Co., Ltd., 1st print published on May 1, 2007, pp. 73-78 with Partial English Translation (10 pages).

K. Saito, "Hikari to Shikisai no Kagaku", Kodansha, Ltd., 1st print published on Oct. 20, 2010, pp. 118-139, with Partial Englsh Translation (21 pages).

The Color Science Association of Japan, ed., "Handbook of Color Science (3rd Edition)", University of Tokyo Press, published in Apr. 2011, pp. 1130-1181, with Partial English Translation (35 pages).

"Names of non-luminous object colours", JIS Z8102, revised Mar. 20, 2001, pp. 1-25 with Partial English Translation (16 pages).

"Colour specification—Names of light-source colours", JIS Z8110, revised Mar. 1, 1995, pp. 1-13, with Partial English Translation (9 pages).

H. Hosoda, "Basics of Photopolymerizable Composite Resins and Clinics", Nippon Shika Shuppan Co., Feb. 10, 1986, pp. 9-20, with Partial English Translation (9 pages).

T. Yamaoka, "Dictionary of Applied Optical Technologies and Materials", published by Industrial Technical Service Center Co., Ltd., Apr. 26, 2006, pp. 108-112, with Partial English Translation (4 pages).

Chemical Society of Japan, ed., "Chemistry Handbook, Fundamentals-II, Third Revision", published by Maruzen, Inc., Jun. 25, 1984, pp. 337-345 (5 pages).

International Search Report including Written Opinion issued in the International Application No. PCT/JP2018/008396, dated Apr. 17, 2018 (20 pages).

J. Yamagawa, "New Standard of Hybrid Arising from Pursuit of Lasting Aesthetics—Hybrid-type Hardness Region (pearl aesthetics)", Japanese Dental Technologists Association, 2011, No. 503, pp. 5-8 (6 pages).

International Search Report including Written Opinion issued in the International Application No. PCT/JP2018/015734, dated Jun. 12, 2018 (15 pages).

Office Action issued in the U.S. Appl. No. 16/605,617, dated Jul. 10, 2020 (12 pages).

International Search Report including Written Opinion issued in the International Application No. PCT/JP2018/015735 dated Jul. 24, 2018 (19 pages).

Office Action issued in the U.S. Appl. No. 16/605,602, dated Jun. 5, 2020 (10 pages).

Extended European Search Report issued in corresponding European Application No. 18763621.2, dated Oct. 22, 2020 (10 pages).

Extended European Search Report issued in corresponding European Application No. 18788652.8, dated Oct. 23, 2020 (8 pages).

Office Action issued in U.S. Appl. No. 16/605,602, dated Dec. 8, 2020 (13 pages).

Extended European Search Report issued in the related EP Patent Application No. EP18787662.8, dated Dec. 17, 2020 (6 pages).

Office Action issued in the related Russian Patent Application No. 2019134976, dated Mar. 23, 2021 (11 pages).

* cited by examiner

CURABLE COMPOSITION

CROSS-REFERENCE TO RELATED APPLICATIONS

This application claims priority to Japanese Patent Application No. 2016-234279 filed on Dec. 1, 2016. The disclosure of this priority application is incorporated in its entirety in the present specification by reference.

TECHNICAL FIELD

The present invention relates to a novel curable composition that is useful for applications such as a dental material, a recording material (an ink, a film, and the like), and a construction material, and particularly for a dental material. More particularly, the present invention relates to a curable composition that can have the external appearance color tone well-controlled without using a dye and a pigment, and does not undergo decoloration and discoloration. Particularly, the present invention relates to a curable composition that can be used as a dental curable composition for a dental filling restorative material that provides excellent convenience and esthetics, and the like.

BACKGROUND ART

In a variety of fields such as dental materials, recording materials, and construction materials, curable compositions including polymerizable monomers and inorganic or organic fillers have been conventionally used. In the field of dental curable compositions, particularly dental filling restorative materials, since curable compositions can impart a color tone equivalent to that of natural tooth color and is easily operable, curable compositions have been rapidly popularized as materials for restoring teeth that have been damaged by dental caries, fracture, and the like. In recent years, from the viewpoint of enhancing the mechanical strength and enhancing the adhesive force to teeth, curable compositions are also used for the restoration of anterior teeth as well as for molar teeth to which high occlusal pressure is exerted.

In recent years, in the field of dental filling restorative materials, there is an increasing demand not only for the recovery of occlusion but also for esthetic restoration of the appearance looking like natural teeth. There is a demand for a restorative material which can reproduce not only simple equivalent color tones but also the transparency or color tone at various restoration sites of teeth.

A natural tooth is formed from dentine and enamel, and the color tone (hue, chroma, and value) varies from site to site. For example, since an incisal part has a thin dentinal layer and is almost covered with enamel, the incisal part is highly transparent. In contrast, the tooth cervix is opaque because the dentinal layer is thick, and compared to an incisal part, the tooth cervix has high value (lightness or darkness of a color) and high chroma (vividness of color). That is, in a natural tooth, the chroma and value decrease in the direction from the tooth cervix where the dentinal layer is thick, toward the incisal part where the dentinal layer is thin. As such, since a tooth has different color tones at different sites, in order to obtain superior esthetic properties for tooth restoration, it is important to prepare a plurality of curable pastes having different color tones, and to select and use, from among those curable pastes, a curable paste having a color tone that is most suitable for the actual restored tooth and teeth adjacent thereto (hereinafter, also referred to as "periphery of the restored tooth") (see, for example, Non-Patent Document 1).

Such selection of color tone is carried out by a dentist, who uses a shade guide (color sample) that includes a collection of various cured product samples of prepared curable pastes, compares the respective color tones of the respective samples with the color tone of the periphery of the restored tooth that is checked by looking into the oral cavity, and selects a color tone that is felt to be closest to the color tone of the periphery of the restored tooth.

Furthermore, as long as it is not the case that the damage of the restored tooth is small with a shallow cavity, it is difficult to realize the adaptation of the color tone by means of filling of a single kind of curable paste. That is, if the cavity is deep (for example, Class 4 cavity), the color tone of a tooth is visually perceived in a state in which not only the color tone of the tooth flank part (enamel portion) but also the color tone of the deep part (dentinal portion) that shows through are combined to give a rich gradation. Therefore, a deep cavity is filled by laminating the curable pastes to be filled, by varying the color tone at a certain interval of depth, and thereby this subtle color tone is reproduced. Usually, this reproduction of color tone is carried out such that a plurality of curable pastes for dentinal restoration, which reproduce the color tones of the dentinal portion, is used and laminated from the deepest part (usually, lamination is continued while each layer is cured), and a curable paste for enamel restoration is laminated at the last surface layer (for example, see Non-Patent Documents 1 and 2).

As such, since there are individual differences and site differences in the color tone of teeth, arranging curable pastes that have their color tones strictly controlled in consideration of these differences, is substantially impossible in reality because a huge number of curable pastes are needed. Furthermore, efforts are needed to select curable pastes having the color tones of teeth from a plurality of thus prepared curable pastes having different color tones.

In addition, pigments or dyes have been conventionally used for the adjustment of the color tone of a curable composition such as a curable paste, and a variety of color tones have been prepared by changing the mixing proportions of pigments or dyes having different color tones. However, the colorability of such pigments or dyes tends to deteriorate over years, causing decoloration or discoloration. In dental filling restorative materials, a phenomenon has frequently occurred, in which the material exhibits high color tone adaptability immediately after restoration but undergoes discoloration with a lapse of time after the restoration, and the external appearance of the restored site does not match that of a natural tooth.

In this regard, as a technology of coloring without using pigments and dyes, utilization of light interference is known in the field of interior construction materials or the field of recording materials (see, for example, Patent Documents 1 and 2).

Patent Document 1: Japanese Unexamined Patent Application, Publication No. 2004-276492
Patent Document 2: Japanese Unexamined Patent Application, Publication No. 2001-239661
Non-Patent Document 1: MATSUMURA, Hideo and TAGAMI, Junji, rev., "Adhesion Yearbook 2006", 1$^{st}$ Edition, Quintessence Publishing Co., Ltd., published in August, 2006, pp. 129-137

Non-Patent Document 2: MIYAZAKI, Masashi, "Science & Technique of Composite Resin Restoration", 1st Edition, Quintessence Publishing Co., Ltd., published in January, 2010, pp. 48-49

DISCLOSURE OF THE INVENTION

Problems to be Solved by the Invention

Restoration of teeth using a curable composition that utilizes colored light brought by interference of light (hereinafter, also referred to as "interfering light") is advantageous because there is no decoloration and discoloration that is seen in the case of using a colorant substance such as a pigment. However, for this restoration, there is a problem that a plurality of curable compositions needs to be prepared in order to adapt to the color tone of a natural tooth having shades in accordance with individual differences or different sites of restoration, and that a plurality of curable compositions having different color tones needs to be used in the case of restoring a deep cavity.

Therefore, an object of the present invention is to provide a curable composition, with which it is not necessary to prepare a plurality of curable compositions having different color tones as described above, a restoration resulting in an external appearance of a cured product to be formed that conforms to the color tone of a natural tooth is enabled, without laminating using a plurality of curable compositions having different color tones, and matching of the cured product to be formed with natural teeth is sustained; and a dental curable composition and a dental filling restorative material, both of which use the composition.

Means for Solving the Problems

In view of the above-described problems, the present inventors have conducted a thorough investigation. As a result, the inventors found that the above-described problems can be solved by using a particular curable composition, and finally completed the present invention.

That is, the curable composition of the present invention is a curable composition including a polymerizable monomer (A), an organic-inorganic composite filler (B), and a polymerization initiator (C), in which the organic-inorganic composite filler (B) includes an organic resin matrix (b1) and a spherical inorganic filler (b2) having an average primary particle size of 230 nm to 1,000 nm, 90% or more of the number of individual particles constituting the spherical inorganic filler (b2) are present in the range of 5% greater or less than the average primary particle size, and the following formulae (1) and (2) are satisfied:

$$nP < nF_{b2} \tag{1}$$

in which nP represents the refractive index of a polymer of the polymerizable monomer (A) at 25° C.; and $nF_{b2}$ represents the refractive index of the spherical inorganic filler (b2) at 25° C., $$nM_{b1} < nF_{b2} \tag{2}$$

in which $nM_{b1}$ represents the refractive index of the organic resin matrix (b1) at 25° C.; and $nF_{b2}$ represents the refractive index of the spherical inorganic filler (b2) at 25° C.

Furthermore, the curable composition of the present invention is a curable composition including a polymerizable monomer (A), an organic-inorganic composite filler (B), and a polymerization initiator (C), in which the organic-inorganic composite filler (B) includes an organic resin matrix (b1) and a spherical inorganic filler (b2) having an average primary particle size of 230 nm to 1,000 nm, 90% or more of the number of individual particles constituting the spherical inorganic filler (b2) are present in the range of 5% greater or less than the average primary particle size, the following formula (1) is satisfied:

$$nP < nF_{b2} \tag{1}$$

in which nP represents the refractive index of a polymer of the polymerizable monomer (A) at 25° C.; and $nF_{b2}$ represents the refractive index of the spherical inorganic filler (b2) at 25° C., and the maximum point of the reflectance obtainable at the time of measuring the spectral reflectance of a cured product having a thickness of 1 mm of the curable composition using a color difference meter on a black background has a wavelength of 550 nm to 770 nm.

Effects of the Invention

The curable composition of the present invention can be used as a dental curable composition, particularly a dental filling restorative material, and the curable composition exhibits color development conforming to the color tones of natural teeth that vary depending on the individual differences or the sites of restoration. Therefore, it is not necessary to prepare a plurality of curable compositions having different color tones, and restoration in which the external appearance of a cured product to be formed conforms to the color tone of a natural tooth is enabled, without laminating using a plurality of curable compositions having different color tones. Furthermore, since the curable composition of the present invention utilizes interfering light, there is no decoloration and discoloration, and matching of a cured product to be formed and natural teeth is sustained.

PREFERRED MODE FOR CARRYING OUT THE INVENTION

The curable composition of the present invention includes a polymerizable monomer (A), an organic-inorganic composite filler (B), and a polymerization initiator (C). Since an organic-inorganic composite filler (B) is incorporated in the curable composition of the present invention, the curable composition has an advantage that there is a reduced feeling of stickiness, and polymerization shrinkage at the time of curing is low.

The biggest feature of the present invention lies in the use of a particular organic-inorganic composite filler (B) in order to achieve convenience of the operability for restoration of a cavity and sustainment of excellent esthetics and matching with natural teeth. This organic-inorganic composite filler (B) includes an organic resin matrix (b1) and a spherical inorganic filler (b2) having an average primary particle size of 230 nm to 1,000 nm, 90% or more of the number of individual particles that constitute the spherical inorganic filler (b2) are present in the range of 5% greater or less than the average primary particle size, and the following formulae (1) and (2) are satisfied:

$$nP < nF_{b2} \tag{1}$$

in which nP represents the refractive index of a polymer of the polymerizable monomer (A) at 25° C.; and $nF_{b2}$ represents the refractive index of the spherical inorganic filler (b2) at 25° C., $$nM_{b1} < nF_{b2} \tag{2}$$

in which $nM_{b1}$ represents the refractive index of the organic resin matrix (b1) at 25° C.; and $nF_{b2}$ represents the refractive index of the spherical inorganic filler (b2) at 25° C.

Thereby, a curable composition that can be used as a dental curable composition, particularly a dental filling restorative material, with which colored light generated by interference of light can be clearly identified even without using a dye and a pigment, and satisfactory color tone adaptability that enables restoration close to natural teeth is provided, can be obtained.

The spherical inorganic filler (b2) has an average primary particle size of 230 nm to 1,000 nm, and 90% or more of the number of individual particles that constitute this spherical inorganic filler (b2) are present in the range of 5% greater or less than the average primary particle size. It is considered that the relationship between the particle size of the spherical inorganic filler (b2) and the phenomenon of light interference conforms to the Bragg's diffraction condition.

In natural teeth, there are individual differences in the color tone, and the color tone also varies depending on the site of restoration. However, the curable composition of the present invention that utilizes the phenomenon of light interference can cope with various color tones. Specifically, in a case in which the chromaticity (hue and chroma) of a foundation tooth is high, external light such as radiated light is absorbed by a background having high chromaticity, and light other than the colored light (interfering light) produced from the dental filling restorative material that utilizes the phenomenon of light interference is suppressed. Therefore, an observation of the colored light can be made. On the other hand, in a case in which the chromaticity of the foundation tooth is low, external light such as radiated light is scattered and reflected by a background having low chromaticity, and since the external light is stronger than the colored light (interfering light) produced from the dental filling restorative material that utilizes the phenomenon of light interference, the external light cancels the colored light. Thus, weak colored light is obtained.

Therefore, since strong colored light is produced in a natural tooth having high chromaticity, and weak colored light is produced in a natural tooth having low chromaticity, wide color tone adaptability can be exhibited with one kind of paste, without using a plurality of pastes having different color tones. As such, it is difficult to achieve the technology of matching the color tone of a natural tooth using one kind of paste irrespective of the level of chromaticity, in the case of a paste that is produced by mixing of coloring substances such as pigments.

The curable composition of the present invention has a feature that a colored light corresponding to the average primary particle size of the spherical inorganic filler (b2) is produced by an interference phenomenon. Whether this colored light is produced or not is verified by measuring the spectral reflectance characteristics of a cured product of the curable composition using a color difference meter under the conditions of both measuring on a black background (backing having a value of 1 according to the Munsell Color System) and measuring on a white background (backing having a value of 9.5 according to the Munsell Color System). On a black background, in a case in which the above-mentioned conditions are satisfied, the light of a particular visible spectrum (wavelength of 380 nm to 780 nm) corresponding to the average primary particle size of the spherical inorganic filler (b2) is clearly identified as a characteristic reflection spectrum depending on the colored light. However, on a white background, a substantially uniform reflectance is exhibited over substantially the entire range of the visible spectrum, and the light of the visible spectrum is not identifiable and is substantially colorless. This is speculated to be because, on a black background, external light (for example, C light source or D65 light source) is absorbed or blocked, and a colored light induced by interference is emphasized; whereas on a white background, since scattered and reflected light of external light is strong, a colored light induced by interference is not easily observed.

In order to exhibit the effect of the present invention of having excellent color tone adaptability, it is important that the relation of the refractive indices is selected so as to satisfy the following formulae (1) and (2).

$$nP < nF_{b2} \quad (1)$$

$$nM_{b1} < nF_{b2} \quad (2)$$

As shown in formula (1), the curable composition of the present invention is such that the relation between the refractive index nP of a polymer of the polymerizable monomer (A) and the refractive index $nF_{b2}$ of the spherical inorganic filler (b2) is $nP < nF_{b2}$, and as shown in formula (2), the relation between the refractive index $nM_{b1}$ of the organic resin matrix (b1) and the refractive index $nF_{b2}$ of the spherical inorganic filler (b2) is $nM_{b1} < nF_{b2}$. In a case in which the refractive index $nF_{b2}$ of the spherical inorganic filler (b2) is high, and the refractive index nP of a polymer of the polymerizable monomer (A) and the refractive index $nM_{b1}$ of the organic resin matrix (b1) are low, interfering light conforming to the Bragg's diffraction conditions is exhibited. However, in an opposite case, light having short wavelengths is more easily subjected to interference, and a colored light thus obtainable has a shorter wavelength and becomes a colored light with a bluish tint. Thus, in a cavity formed over from the enamel to the dentine, the color tone adaptability to dentine is likely to become defective.

Meanwhile, a cured product of the curable composition of the present invention exhibits a yellow to reddish (for example, wavelength of 550 nm to 770 nm) colored light according to the average primary particle size of the spherical inorganic filler (b2). Therefore, a curable composition that satisfies the conditions of the above-described formulae (1) and (2) may be "a curable composition that satisfies the conditions of formula (1) described above, with which when the spectral reflectance of a cured product having a thickness of 1 mm of the curable composition is measured using a color difference meter on a black background (that is, using a backing with a value of 1 according to the Munsell Color System as the background), the maximum point of the reflectance has a wavelength (peak wavelength) of 550 nm to 770 nm".

In the following description, various components of the curable composition of the present invention will be explained.

<Polymerizable Monomer (A)>

Regarding the polymerizable monomer, any known polymerizable monomer can be used without any particular limitations. From the viewpoint of the polymerization rate, a radical polymerizable or cationic polymerizable monomer is preferred. A particularly preferred radical polymerizable monomer is a (meth)acrylic compound, and examples include (meth)acrylates listed below. Furthermore, particularly preferred examples of the cationic polymerizable monomer include epoxies and oxetanes.

Generally, examples of (meth)acrylates as (meth)acrylic compounds that are suitably used, include compounds shown in the following (I) to (IV).

(I) Monofunctional Polymerizable Monomer
(I-i) Compound that does not have Acidic Group and Hydroxy Group
methyl (meth)acrylate,
ethyl (meth)acrylate,
n-butyl (meth)acrylate,
2-ethylhexyl (meth)acrylate,
n-lauryl (meth)acrylate,
n-stearyl (meth)acrylate,
tetrafurfuryl (meth)acrylate,
glycidyl (meth)acrylate,
methoxyethylene glycol (meth)acrylate,
methoxydiethylene glycol (meth)acrylate,
methoxytriethylene glycol (meth)acrylate,
methoxypolyethylene glycol (meth)acrylate,
ethoxyethylene glycol (meth)acrylate,
ethoxydiethylene glycol (meth)acrylate,
ethoxytriethylene glycol (meth)acrylate,
ethoxypolyethylene glycol (meth)acrylate,
phenoxyethylene glycol (meth)acrylate,
phenoxydiethylene glycol (meth)acrylate,
phenoxytriethylene glycol (meth)acrylate,
phenoxypolyethylene glycol (meth)acrylate,
cyclohexyl (meth)acrylate,
benzyl (meth)acrylate,
isobornyl (meth)acrylate,
trifluoroethyl (meth)acrylate, and the like.
(I-ii) Compound Having Acidic Group
(meth)acrylic acid,
N-(meth)acryloyl glycine,
N-(meth)acryloyl aspartic acid,
N-(meth)acryloyl-5-aminosalicylic acid,
2-(meth)acryloyloxyethyl hydrogen succinate,
2-(meth)acryloyloxyethyl hydrogen phthalate,
2-(meth)acryloyloxyethyl hydrogen malate,
6-(meth)acryloyloxyethyl naphthalene-1,2,6-tricarboxylic acid,
O-(meth)acryloyl tyrosine,
N-(meth)acryloyl tyrosine,
N-(meth)acryloyl phenylalanine,
N-(meth)acryloyl-p-aminobenzoic acid,
N-(meth)acryloyl-o-aminobenzoic acid,
p-vinylbenzoic acid,
2-(meth)acryloyloxybenzoic acid,
3-(meth)acryloyloxybenzoic acid,
4-(meth)acryloyloxybenzoic acid,
N-(meth)acryloyl-5-aminosalicylic acid,
N-(meth)acryloyl-4-aminosalicylic acid, and the like and compounds obtained by converting carboxyl groups of these compounds to acid anhydride groups;
11-(meth)acryloyloxyundecane-1,1-dicarboxylic acid,
10-(meth)acryloyloxydecane-1,1-dicarboxylic acid,
12-(meth)acryloyloxydodecane-1,1-dicarboxylic acid,
6-(meth)acryloyloxyhexane-1,1-dicarboxylic acid,
2-(meth)acryloyloxyethyl-3'-methacryloyloxy-2'-(3,4-dicarboxybenzoyloxy)propyl succinate,
4-(2-(meth)acryloyloxyethyl) trimellitate anhydride,
4-(2-(meth)acryloyloxyethyl) trimellitate,
4-(meth)acryloyloxyethyl trimellitate,
4-(meth)acryloyloxybutyl trimellitate,
4-(meth)acryloyloxyhexyl trimellitate,
4-(meth)acryloyloxydecyl trimellitate,
4-(meth)acryloyloxybutyl trimellitate,
6-(meth)acryloyloxyethyl naphthalene-1,2,6-tricarboxylic acid anhydride,
6-(meth)acryloyloxyethyl naphthalene-2,3,6-tricarboxylic acid anhydride,
4-(meth)acryloyloxyethylcarbonylpropionoyl-1,8-naphthalic anhydride,
4-(meth)acryloyloxyethylnaphthalene-1,8-tricarboxylic acid anhydride,
9-(meth)acryloyloxynonane-1,1-dicarboxylic acid,
13-(meth)acryloyloxytridecane-1,1-dicarboxylic acid,
11-(meth)acrylamidoundecane-1,1-dicarboxylic acid,
2-(meth)acryloyloxyethyl dihydrogen phosphate,
2-(meth)acryloyloxyethylphenyl hydrogen phosphate,
10-(meth)acryloyloxydecyl dihydrogen phosphate,
6-(meth)acryloyloxyhexyl dihydrogen phosphate,
2-(meth)acryloyloxyethyl-2-bromoethyl hydrogen phosphate,
2-(meth)acrylamidoethyl dihydrogen phosphate,
2-(meth)acrylamido-2-methylpropanesulfonic acid,
10-sulfodecyl (meth)acrylate,
3-(meth)acryloxypropyl-3-phosphonopropionate,
3-(meth)acryloxypropyl phosphonoacetate,
4-(meth)acryloxybutyl-3-phosphonopropionate,
4-(meth)acryloxybutyl phosphonoacetate,
5-(meth)acryloxypentyl-3-phosphonopropionate,
5-(meth)acryloxypentyl phosphonoacetate,
6-(meth)acryloxyhexyl-3-phosphonopropionate,
6-(meth)acryloxyhexyl phosphonoacetate,
10-(meth)acryloxydecyl-3-phosphonopropionate,
10-(meth)acryloxydecyl phosphonoacetate,
2-(meth)acryloyloxyethylphenyl phosphonate,
2-(meth)acryloyloxyethylphosphonic acid,
10-(meth)acryloyloxydecylphosphonic acid,
N-(meth)acryloyl-w-aminopropylphosphonic acid,
2-(meth)acryloyloxyethylphenyl hydrogen phosphate,
2-(meth)acryloyloxyethyl-2'-bromoethyl hydrogen phosphate,
2-(meth)acryloyloxyethylphenyl phosphonate, and the like.
(I-iii) Compound Having Hydroxy Group
2-hydroxyethyl (meth)acrylate,
3-hydroxypropyl (meth)acrylate,
4-hydroxybutyl (meth)acrylate,
6-hydroxyhexyl (meth)acrylate,
10-hydroxydecyl (meth)acrylate,
propylene glycol mono(meth)acrylate,
glycerol mono(meth)acrylate,
erythritol mono(meth)acrylate,
N-methylol (meth)acrylamide,
N-hydroxyethyl (meth)acrylamide,
N,N-(dihydroxyethyl) (meth)acrylamide, and the like.
(II) Bifunctional Polymerizable Monomer
(II-i) Aromatic Compound-Based Monomer
2,2-bis(methacryloyloxyphenyl)propane,
2,2-bis[(3-methacryloyloxy-2-hydroxypropyloxy)phenyl] propane,
2,2-bis(4-methacryloyloxyphenyl)propane,
2,2-bis(4-methacryloyloxypolyethoxyphenyl)propane,
2,2-bis(4-methacryloyloxydiethoxyphenyl)propane,
2,2-bis(4-methacryloyloxytetraethoxyphenyl)propane,
2,2-bis(4-methacryloyloxypentaethoxyphenyl)propane,
2,2-bis(4-methacryloyloxydipropoxyphenyl)propane,
2(4-methacryloyloxydiethoxyphenyl)-2(4-methacryloyloxytriethoxyphenyl)propane,
2(4-methacryloyloxydipropoxyphenyl)-2-(4-methacryloyloxytriethoxyphenyl)propane,
2,2-bis(4-methacryloyloxypropoxyphenyl)propane,
2,2-bis(4-methacryloyloxyisopropoxyphenyl)propane, and the like
and acrylates corresponding to these methacrylates;
diadducts obtainable from addition of vinyl monomers having an —OH group, such as methacrylates such as 2-hydroxyethyl methacrylate, 2-hydroxypropyl methacrylate, and 3-chloro-2-hydroxypropyl methacrylate, or acrylates corresponding to these methacrylates, and diisocyanate compounds having an aromatic group, such as methylbenzene diisocyanate and 4,4'-diphenylmethane diisocyanate; di(methacryloxyethyl)diphenylmethanediurethane, and the like.

(II-ii) Aliphatic Compound-Based Monomer
ethylene glycol dimethacrylate,
diethylene glycol dimethacrylate,
triethylene glycol dimethacrylate,
tetraethylene glycol dimethacrylate,
neopentyl glycol dimethacrylate,
1,3-butanediol dimethacrylate,
1,4-butanediol dimethacrylate,
1,6-hexanediol dimethacrylate, and the like
and acrylates corresponding to these methacrylates;
diadducts obtainable from addition products of vinyl monomers having an —OH group, such as 2-hydroxyethyl methacrylate, 2-hydroxypropyl methacrylate, and 3-chloro-2-hydroxypropyl methacrylate, or acrylates corresponding to these methacrylates, and diisocyanate compounds such as hexamethylene diisocyanate, trimethylhexamethylene diisocyanate, methylcyclohexane diisocyanate, isophorone diisocyanate, and methylenebis(4-cyclohexyl isocyanate), for example, 1,6-bis(methacrylethyloxycarbonylamino)trimethylhexane; 1,2-bis(3-methacryloyloxy-2-hydroxypropoxy)ethyl, and the like.

(III) Trifunctional Polymerizable Monomer
trimethylolpropane trimethacrylate,
trimethylolethane trimethacrylate,
pentaerythritol trimethacrylate,
trimethylolmethane trimethacrylate, and the like
and acrylates corresponding to these methacrylates, and the like.

(IV) Tetrafunctional Polymerizable Monomer
pentaerythritol tetramethacrylate,
pentaerythritol tetraacrylate;
diadducts obtainable from addition products of diisocyanate compounds such as methylbenzene diisocyanate, methylcyclohexane diisocyanate, isophorone diisocyanate, hexamethylene diisocyanate, trimethylhexamethylene diisocyanate, methylenebis(4-cyclohexyl isocyanate), 4,4-diphenylmethane diisocyanate, and tolylene-2,4-diisocyanate, and glycidol dimethacrylate, and the like.

Regarding these (meth)acrylate-based polymerizable monomers, a plurality of kinds of compounds may be used in combination, if necessary.

Furthermore, if necessary, a polymerizable monomer other than the above-described (meth)acrylate-based monomers may also be used.

According to the present invention, regarding the polymerizable monomer (A), generally, a plurality of polymerizable monomers is used due to the regulation of the physical properties (mechanical characteristics and adhesiveness to dentine in dental use applications) of a cured product of the curable composition. At that time, it is desirable that the type and amount of the polymerizable monomer are set such that the refractive index of the polymerizable monomer (A) at 25° C. falls in the range of 1.38 to 1.55, from the viewpoint of the difference between the refractive index of the polymerizable monomer and the refractive index of the spherical inorganic filler (b2) constituting the organic-inorganic composite filler (B) that will be described below. That is, in a case in which a silica-titanium group element oxide-based composite oxide, which enables easy adjustment of the refractive index, is used as the spherical inorganic filler (b2), the refractive index $nF_{b2}$ of the spherical inorganic filler is in the range of about 1.45 to 1.58 depending on the content of the silica portion, and by setting the refractive index of the polymerizable monomer (A) to be in the range of 1.38 to 1.55, the refractive index nP of the polymer obtainable from the polymerizable monomer (A) can be set to be approximately in the range of 1.40 to 1.57. Thus, it is easy to satisfy formula (1). Meanwhile, in the case of using a plurality of kinds of polymerizable monomers as the polymerizable monomer (A), it is desirable that the refractive index of a mixture obtained by mixing the plurality of kinds of polymerizable monomers is in the above-mentioned range, and the individual polymerizable monomers may not necessarily have their refractive indices in the above-described range.

Meanwhile, the refractive index of a polymerizable monomer or a cured product of a polymerizable monomer can be determined using an Abbe refractometer at 25° C.

<Organic-Inorganic Composite Filler (B)>

According to the present invention, the organic-inorganic composite filler (B) includes an organic resin matrix (b1) and a spherical inorganic filler (b2) having an average primary particle size of 230 nm to 1,000 nm.

The biggest feature of the present invention lies in that the spherical inorganic filler (b2) having an average primary particle size of 230 nm to 1,000 nm, which constitutes the organic-inorganic composite filler (B), is spherical in shape, 90% or more of the number of individual particles are present in the range of 5% greater or less than the average primary particle size, and the relationship between the refractive index nP of a polymer of the polymerizable monomer component (A) and the refractive index $nF_{b2}$ of the spherical inorganic filler (b2) as represented by the following formula (1), and the relationship between the refractive index $nM_{b1}$ of the organic resin matrix (b1) and the refractive index $nF_{b2}$ of the spherical inorganic filler (b2) as represented by the following formula (2), are satisfied.

$$nP < nF_{b2} \quad (1)$$

$$nM_{b1} < nF_{b2} \quad (2)$$

Thereby, a curable composition that can be used as a dental curable composition, particularly a dental filling restorative material, with which a colored light caused by light interference can be clearly identified even without using a dye and a pigment, and satisfactory color tone adaptability that enables restoration close to a natural tooth is provided, can be obtained.

One feature of the curable composition of the present invention is that the particle size distribution of the spherical inorganic filler (b2) that constitutes the organic-inorganic composite filler (B) is narrow. A colored light induced by interference is produced when the constituent particles are regularly accumulated. Therefore, since the spherical inorganic filler (b2) is spherical in shape, and the particle size distribution is narrow, a colored light induced by interference is produced. On the other hand, in the case of irregularly shaped particles produced by pulverization or the like, since the particle size distribution is broad, and the shape is non-uniform, the particles are not regularly accumulated, and colored light is not produced.

As described above, for the spherical inorganic filler (b2), it is important that the average primary particle size of the filler is 230 nm to 1,000 nm, and 90% or more (number of particles) of the individual particles constituting the spherical inorganic filler (b2) are present in the range of 5% greater or less than the average primary particle size. That is, the spherical inorganic filler (b2) is composed of a plurality of primary particles, and in the range of 5% greater or less than the average particle size of the multiple primary particles, primary particles in a number of 90% or more among all of the primary particles are present. Exhibition of a colored light induced by interference is achieved as diffraction and interference occur according to the Bragg's condition, and light having a particular wavelength is emphasized. Thus, when particles of the above-mentioned particle size are incorporated, a cured product of the curable composition exhibits a yellow to reddish colored light depending on the particle size. From the viewpoint of obtaining excellent color tone adaptability to dentine in a cavity formed over from the enamel to the dentine, the wavelength of the colored light is preferably 550 nm to 770 nm.

From the viewpoint of further enhancing the effect of exhibiting a colored light induced by interference, the average primary particle size of the spherical inorganic filler (b2) is suitably 230 nm to 800 nm, more suitably 230 nm to 500 nm, even more suitably 230 nm to 350 nm, and particularly suitably 260 nm to 350 nm. In a case in which a spherical inorganic filler having an average primary particle size in the range of 150 nm to 230 nm is used, the colored light thus obtainable is bluish, and in a cavity formed over from the enamel to the dentine, the color tone adaptability to dentine is likely to be poor. Furthermore, in a case in which a spherical inorganic filler having an average primary particle size of less than 100 nm is used, the phenomenon of interference by visible light is not likely to occur. On the other hand, in a case in which a spherical inorganic filler having an average primary particle size of larger than 1,000 nm is used, exhibition of the phenomenon of light interference can be expected; however, in a case in which the curable composition of the present invention is used as a restorative material for dental filling, problems such as sedimentation of the spherical inorganic filler and deterioration of abradability occur, which is not preferable.

The curable composition of the present invention exhibits various colored lights according to the particle size of the spherical inorganic filler (b2). Therefore, in order to obtain light having a desired color, the average primary particle size of the spherical inorganic filler (b2) may be decided from the range of 230 nm to 1,000 nm. In a case in which a spherical inorganic filler having an average primary particle size in the range of 230 nm to 260 nm is used, the colored light thus obtainable is yellowish, and the curable composition is useful for the restoration of teeth having a color in the class of B system (red-yellow) according to Shade Guide "VITAPAN Classical", and is particularly useful for the restoration of a cavity formed over from the enamel to the dentine. In a case in which a spherical inorganic filler having an average primary particle size in the range of 260 nm to 350 nm is used, the colored light thus obtainable is reddish, and the curable composition useful for the restoration of teeth having a color in the class of A system (red-brown) according to Shade Guide "VITAPAN Classical", and is particularly useful for the restoration of a cavity formed over from the enamel to the dentine. Since the hue of the dentine is reddish as such in many cases, an embodiment of using a spherical inorganic filler having an average primary particle size in the range of 260 nm to 350 nm is most preferable because adaptability to restored teeth having a variety of color tones is improved to a large extent. On the other hand, in a case in which a spherical inorganic filler having an average primary particle size in the range of 150 nm to 230 nm is used, the colored light thus obtainable is bluish, and the color tone adaptability to dentine is likely to be poor in a cavity formed over from the enamel to the dentine, as described above. However, the curable composition is useful for the restoration of the enamel, and is particularly useful for the restoration of an incisal part.

It is important that the spherical inorganic filler (b2) has an average primary particle size in the above-described range.

According to the present invention, the average primary particle sizes of the spherical inorganic filler (b2) and the spherical inorganic filler (D) that will be described below refer to values each obtained by taking a photograph of the powder by scanning electron microscopy, selecting thirty or more particles observed within a unit viewing field of the photograph, determining the particle sizes (maximum diameters) of the respective particles, and calculating the average value.

Furthermore, according to the present invention, the spherical shape of the spherical inorganic filler (b2) and the spherical inorganic filler (D) that will be described below may be approximately spherical, and it is not necessarily essential to be a perfect true sphere. The average uniformity obtained by taking a photograph of particles by scanning electron microscopy, measuring the maximum diameters for the respective particles (thirty or more particles) within a unit viewing field of the photograph, and dividing the particle size in a direction orthogonally intersecting the maximum diameter by the maximum diameter, is desirably 0.6 or higher, and more preferably 0.8 or higher.

As described above, a colored light induced by interference is exhibited with high color tone adaptability to natural teeth in a case in which the following formulae (1) and (2) are satisfied:

$$nP < nF_{b2} \quad (1)$$

in which nP represents the refractive index of a polymer of the polymerizable monomer (A) at 25° C.; and $nF_{b2}$ represents the refractive index of the spherical inorganic filler (b2) at 25° C., $$nM_{b1} < nF_{b2} \quad (2)$$

in which $nM_{b1}$ represents the refractive index of the organic resin matrix (b1) at 25° C.; and $nF_{b2}$ represents the refractive index of the spherical inorganic filler (b2) at 25° C.

That is, the refractive index $nF_{b2}$ of the spherical inorganic filler (b2) is in a state of being higher than the refractive index nP of a polymer of the polymerizable monomer (A) and the refractive index $nM_{b1}$ of the organic resin matrix (b1).

In a case in which the curable composition of the present invention is used as a dental curable composition, in order to realize a color tone adaptability that is capable of restoration close to natural teeth, the difference in the refractive index between the refractive index $nF_{b2}$ of the spherical inorganic filler (b2) and the refractive index nP of a polymer of the polymerizable monomer (A), and the difference in the refractive index between the refractive index $nF_{b2}$ of the spherical inorganic filler (b2) and the refractive index $nM_{b1}$ of the organic resin matrix (b1) are preferably adjusted to 0.001 or greater, and more preferably adjusted to 0.002 or greater.

Furthermore, in a case in which a cured product of the curable composition of the present invention has adequate transparency, a colored light induced by interference is clearly exhibited, and the color tone adaptability is enhanced. Therefore, the difference in the refractive index between the refractive index $nF_{b2}$ of the spherical inorganic filler (b2) and the refractive index nP of a polymer of the polymerizable monomer (A), and the difference in the refractive index between the refractive index $nF_{b2}$ of the spherical inorganic filler (b2) and the refractive index $nM_{b1}$ of the organic resin matrix (b1) are preferably adjusted to 0.1 or less, and more preferably to 0.05 or less, and it is desirable that transparency is not impaired as far as possible.

Regarding the spherical inorganic filler (b2), any spherical inorganic filler used as a component for a curable composition can be used without limitations. Specific examples include inorganic powders such as amorphous silica, silica-titanium group element oxide-based composite oxide particles (silica-zirconia, silica-titania, or the like), quartz, alumina, barium glass, strontium glass, lanthanum glass, fluoroaluminosilicate glass, ytterbium fluoride, zirconia, titania, and colloidal silica.

Among these, from the viewpoint that the adjustment of the refractive index of the filler is easy, silica-titanium group element oxide-based composite oxide particles are preferred.

The silica-titanium group element oxide-based composite oxide particles according to the present invention are composite oxides of silica and titanium group element (elements of Group 4 in the Periodic Table of Elements) oxides, and examples include silica-titania, silica-zirconia, and silica-titania-zirconia. Above all, from the viewpoint that adjustment of the refractive index of the filler is enabled, and high opacity to X-rays can be imparted, silica-zirconia is preferred. The composite ratio is not particularly limited; however, from the viewpoint of imparting sufficient opacity to X-rays and adjusting the refractive index to the suitable range that will be described below, it is preferable that the percentage content of silica is 70 mol % to 95 mol %, and the percentage content of the titanium group element oxide is 5 mol % to 30 mol %. In the case of silica-zirconia, the refractive index can be freely changed by changing the respective composite ratios as such.

Meanwhile, in these silica-titanium group element oxide-based composite oxide particles, compounding of a metal oxide other than silica and a titanium group element oxide is also allowed, as long as the amount is small. Specifically, an alkali metal oxide such as sodium oxide or lithium oxide may also be incorporated in an amount of 10 mol % or less.

The method for producing the silica-titanium group element oxide-based composite oxide particles is not particularly limited; however, in order to obtain the particular spherical inorganic filler of the present invention, for example, a so-called sol-gel method of adding a mixed solution including a hydrolyzable organosilicon compound and a hydrolyzable organotitanium group metal compound to an alkaline solvent, performing hydrolysis, and precipitating a reaction product, is suitably employed.

These silica-titanium group element oxide-based composite oxide particles may be surface-treated with a silane coupling agent. Through a surface treatment using a silane coupling agent, when the composite oxide particles are produced into an organic-inorganic composite filler, excellent interfacial strength between the composite filler and the organic resin matrix (b1) is obtained. Representative examples of the silane coupling agent include organosilicon compounds such as γ-methacryloyloxyalkyltrimethoxysilane and hexamethyldisilazane. The amount of surface treatment with these silane coupling agents is not particularly limited, and an optimal value may be decided after the mechanical properties and the like of a cured product of the curable composition thus obtainable are checked in advance by experiments. An example of a suitable range is the range of 0.1 to 15 parts by mass with respect to 100 parts by mass of the spherical inorganic filler (b2).

The percentage content of the spherical inorganic filler (b2) in the organic-inorganic composite filler (B) is preferably 30% to 95% by mass. When the percentage content of the spherical inorganic filler (b2) is 30% by mass or more, the colored light of a cured product of the curable composition is exhibited satisfactorily, and the mechanical strength can also be sufficiently increased. Meanwhile, it is difficult in view of operation to adjust the percentage content of the spherical inorganic filler (b2) to be more than 95% by mass. The percentage content of the spherical inorganic filler (b2) in the organic-inorganic composite filler (B) is more preferably 40% to 90% by mass.

In the spherical inorganic filler (b2), the refractive index of the silica-titanium group element oxide-based composite oxide, with which the adjustment of the refractive index is easy, is in the range of about 1.45 to 1.58 according to the content of the silica portion. That is, in a case in which a silica-titanium group element oxide-based composite oxide is used as the spherical inorganic filler (b2), by having the refractive index of the polymerizable monomer (A) set to be in the above-mentioned range (in the range of 1.38 to 1.55), the refractive index nP of a polymer obtainable from the polymerizable monomer (A) can be set approximately to the range of 1.40 to 1.57. Therefore, the spherical inorganic filler (b2) can be easily selected so as to satisfy the above-mentioned condition (formula (1)). That is, it is desirable to use a silica-titanium group element oxide-based composite oxide (silica-titania, silica-zirconia, or the like) including an appropriate amount of silica portion.

With regard to the organic-inorganic composite filler (B), as the organic resin matrix (b1), a homopolymer or a copolymer of a plurality of kinds obtainable by using the same polymerizable monomers as those described as the above-mentioned polymerizable monomer (A) can be selected without limitations. As described above, in a case in which a silica-titanium group element oxide-based composite oxide, with which the adjustment of the refractive index is easy, is used as the spherical inorganic filler (b2), the refractive index is adjusted to be in the range of about 1.45 to 1.58 according to the content of the silica portion. Therefore, by setting the refractive index $nM_{b1}$ of the organic resin matrix (b1) to be approximately in the range of 1.40 to 1.57, the above-mentioned condition (formula (2)) can be satisfied.

The organic resin matrix (b1) may be the same as or different from the polymer obtainable from the polymerizable monomer (A); however, the difference in the refractive index between the refractive index $nM_{b1}$ of the organic resin matrix (b1) and the refractive index nP of a polymer of the polymerizable monomer (A) is preferably 0.005 or less from the viewpoint of transparency of the curable composition thus obtainable. When the difference in the refractive index is adjusted to be 0.005 or less, transparency is increased, and attenuation of the colored light induced by interference tends to be suppressed. Furthermore, from the viewpoint that light diffusibility can be imparted by a difference in the refractive index, and the color tone adaptability between the curable composition and teeth can be enhanced, the difference in the refractive index is more preferably in the range of 0.001 to 0.005.

The method for producing the organic-inorganic composite filler (B) is not particularly limited, and for example, a general production method of mixing predetermined amounts of the respective components of the spherical inorganic filler (b2), the polymerizable monomer, and a polymerization initiator, polymerizing the components by a method such as heating or light irradiation, and then pulverizing the resultant, can be employed. Alternatively, the production method described in PCT International Publication No. WO 2011/115007 or PCT International Publication No. WO 2013/039169 can also be employed. In this production method, inorganic aggregated particles formed as a result of aggregation of the spherical inorganic filler (b2) are immersed in a polymerizable monomer solvent including a polymerizable monomer, a polymerization initiator, and an organic solvent, subsequently the organic solvent is removed, and the polymerizable monomer is polymerized and cured by a method such as heating or light irradiation. According to the production method described in PCT International Publication No. WO 2011/115007 or PCT International Publication No. WO 2013/039169, an organic-inorganic composite filler having an organic resin phase that covers the surface of the respective inorganic primary particles of inorganic aggregated particles formed as a result of aggregation of inorganic primary particles and also binds the respective inorganic primary particles with one another, and having cohesion gaps formed between the organic resin phase covering the surface of the respective inorganic primary particles, is obtained. As the polymerization initiator, any known polymerization initiator may be used without particular limitations; however, from the viewpoint that a cured product having a lower degree of yellowness can be obtained, it is preferable to use a thermal polymerization initiator, and it is more preferable to use a thermal polymerization initiator formed from a compound that does not have an aromatic ring in the structure.

Particularly, in a polymerization process or a process of pulverizing the cured product thus obtained, the organic component in the organic-inorganic composite filler undergoes color change due to friction-induced heat or the like, and an organic-inorganic composite filler having a high degree of yellowness is obtained. A curable composition that uses such an organic-inorganic composite filler produces a cured product having a high degree of yellowness. The degree of yellowness of a cured product of a curable composition affects the hue of the colored light identified from a material having a colored light induced by interference as in the case of the present invention.

Therefore, according to the present invention, it is preferable that the organic-inorganic composite filler (B) has a low degree of yellowness. Specifically, b* representing blue to yellow in the CIELab is preferably −2.5 or less, and more preferably −3.0 or less, on a black background color.

The average particle size of the organic-inorganic composite filler (B) is not particularly limited; however, from the viewpoint of improving the mechanical strength of the cured product and the manipulability of the curable paste, the average particle size is preferably 2 μm to 100 μm, more preferably 5 μm to 50 μm, and even more preferably 5 μm to 30 μm. Furthermore, the shape is not particularly limited, and an irregular shape obtainable by mixing predetermined amounts of the respective components of the spherical inorganic filler (b2), the polymerizable monomer, and the polymerization initiator, polymerizing the components by a method such as heating or light irradiation, and then pulverizing the resultant, or a spherical shape or an approximately spherical shape produced by the method described in PCT International Publication No. WO 2011/115007 or PCT International Publication No. WO 2013/039169 may be mentioned.

The organic-inorganic composite filler (B) may include known additives to the extent that the effects are not inhibited. Specific examples of the additives include a pigment, a polymerization inhibitor, and a fluorescent brightening agent. These additives are each used at a proportion of usually 0.0001 to 5 parts by mass with respect to 100 parts by mass of the organic-inorganic composite filler.

Furthermore, the organic-inorganic composite filler (B) may be subjected to washing or a surface treatment using a silane coupling agent or the like.

The content of the organic-inorganic composite filler (B) is preferably 50 to 1,000 parts by mass with respect to 100 parts by mass of the polymerizable monomer (A). In order to improve the manipulability of a paste of the curable composition and the mechanical strength of the cured product by means of incorporation of the organic-inorganic composite filler (B), the content of the organic-inorganic composite filler (B) is more preferably 70 to 600 parts by mass, and even more preferably 100 to 400 parts by mass, with respect to 100 parts by mass of the polymerizable monomer (A).

<Polymerization Initiator (C)>

The polymerization initiator is incorporated for the purpose of polymerizing and curing the present composition, and any known polymerization initiator is used without particular limitations.

Above all, for a dental direct filling restoration use application where the composition is often cured within the oral cavity, a photopolymerization initiator or a chemical polymerization initiator is preferred, and from the viewpoint that a mixing operation is unnecessary, and the operation is convenient, a photopolymerization initiator is more preferred.

Regarding the polymerization initiator used for photopolymerization, benzoin alkyl ethers such as benzoin methyl ether, benzoin ethyl ether, and benzoin isopropyl ether; benzyl ketals such as benzyl dimethyl ketal and benzyl diethyl ketal; benzophenones such as benzophenone, 4,4'-dimethylbenzophenone, and 4-methacryloxybenzophenone; α-diketones such as diacetyl, 2,3-pentadionebenzyl, camphor-quinone, 9,10-phenanthraquinone, and 9,10-anthraquinone; thioxanthone compounds such as 2,4-diethoxythioxanthone, 2-chlorothioxanthone, and methylthioxanthone; and bisacylphosphine oxides such as bis-(2,6-dichlorobenzoyl)phenylphosphine oxide, bis(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, and bis(2,4,6-trimethylbenzoyl)-phenylphosphine oxide, and the like can be used.

Meanwhile, as the photopolymerization initiator, a reducing agent is frequently added, and examples thereof include tertiary amines such as 2-(dimethylamino)ethyl methacrylate, ethyl 4-dimethylaminobenzoate, and N-methyldiethanolamine; aldehydes such as lauryl aldehyde, dimethylaminobenzaldehyde, and terephthalic aldehyde; and sulfur-containing compounds such as 2-mercaptobenzoxazole, 1-decanethiol, thiosalicylic acid, and thiobenzoic acid.

Furthermore, cases of using a composition by adding a photoacid generator, in addition to the photopolymerization initiator and the reducing compound, may be frequently seen. Examples of such a photoacid generator include a diaryliodonium salt-based compound, a sulfonium salt-based compound, a sulfonic acid ester compound, a halomethyl-substituted-S-triazine derivative, and a pyridinium salt-based compound.

These polymerization initiators may be used singly, or two or more kinds thereof may be used as mixtures. Regarding the content of the polymerization initiator, an effective amount may be selected according to the purpose; however, the polymerization initiator is usually used at a proportion of 0.01 to 10 parts by mass, and preferably at a proportion of 0.1 to 5 parts by mass, with respect to 100 parts by mass of the polymerizable monomer (A).

<Spherical Inorganic Filler (D)>

In the curable composition of the present invention, for the purpose of effectively exhibiting a colored light induced by interference of the cured product and further improving the color tone adaptability, a spherical inorganic filler (D) having an average primary particle size of 230 nm to 1,000 nm can be further incorporated in addition to the organic-inorganic composite filler (B). The spherical inorganic filler (D) is such that, similarly to the spherical inorganic filler (b2), 90% or more of the number of individual constituent particles are present in the range of 5% greater or less than the average primary particle size, and the following formulae (3) and (4) are satisfied:

$$nP < nF_D \quad (3)$$

in which nP represents the refractive index of a polymer of the polymerizable monomer (A) at 25° C.; and $nF_D$ represents the refractive index of the spherical inorganic filler (D) at 25° C., $$nM_{b1} < nF_D \quad (4)$$

in which $nM_{b1}$ represents the refractive index of the organic resin matrix (b1) at 25° C.; and $nF_D$ represents the refractive index of the spherical inorganic filler (D) at 25° C.

The particle properties of the spherical inorganic filler (D) are similar to those of the spherical inorganic filler (b2) that constitutes the organic-inorganic composite filler (B) described above.

The spherical inorganic filler (D) is spherical and has a narrow particle size distribution, similarly to the spherical inorganic filler (b2). Therefore, a colored light induced by interference is also produced by the spherical inorganic filler (D).

Regarding the spherical inorganic filler (D), it is important that the average primary particle size is 230 nm to 1,000 nm, and 90% (number of particles) or more of the individual particles that constitute the spherical inorganic filler (D) are present in the range of 5% greater or less than the average primary particle size. That is, the spherical inorganic filler (D) is composed of a plurality of primary particles, and in the range of 5% greater or less than the average particle size of the multiple primary particles, primary particles in a number of 90% or more among all of the primary particles are present. Exhibition of a colored light induced by interference is brought about as diffraction and interference occur according to the Bragg's condition, and light having a particular wavelength is emphasized. Thus, when particles having the above-described particle size are incorporated, a cured product of the curable composition exhibits a yellow to reddish colored light due to the particle size. From the viewpoint of obtaining excellent color tone adaptability to dentine in a cavity formed over from the enamel to the dentine, the wavelength of the colored light is preferably 550 nm to 770 nm.

From the viewpoint of further enhancing the effect of exhibiting a colored light induced by interference, the average primary particle size of the spherical inorganic filler (D) is suitably 230 nm to 800 nm, more suitably 230 nm to 500 nm, even more suitably 230 nm to 350 nm, and particularly suitably 260 nm to 350 nm. In a case in which a spherical inorganic filler having an average primary particle size in the range of 150 nm to 230 nm is used, the colored light thus obtainable is bluish, and in a cavity formed over from the enamel to the dentine, the color tone adaptability to the dentine is likely to be defective. Furthermore, in a case in which a spherical inorganic filler having an average primary particle size of less than 100 nm is used, the phenomenon of interference of visible light does not easily occur. On the other hand, in a case in which a spherical inorganic filler having an average primary particle size of greater than 1,000 nm is used, exhibition of the phenomenon of light interference can be expected; however, in a case in which the curable composition of the present invention is used as a dental filling restorative material, problems such as sedimentation of the spherical inorganic filler and deterioration of abradability occur, which is not preferable.

The curable composition of the present invention having the spherical inorganic filler (D) incorporated therein exhibits various colored lights as described above, depending on the particle sizes of the spherical inorganic filler (b2) and the spherical inorganic filler (D). In a case in which a spherical inorganic filler having an average primary particle size in the range of 230 nm to 260 nm is used, the colored light thus obtainable is yellowish, and the curable composition is useful for the restoration of teeth having a color in the class of B system (red-yellow) according to Shade Guide "VITAPAN Classical", and is particularly useful for the restoration of a cavity formed over from the enamel to the dentine. In a case in which a spherical inorganic filler having an average primary particle size in the range of 260 nm to 350 nm is used, the colored light thus obtainable is reddish, and the curable composition is useful for the restoration of teeth having a color in the class of A system (red-brown) according to Shade Guide "VITAPAN Classical", and is particularly useful for the restoration of a cavity formed over from the enamel to the dentine. On the other hand, in a case in which a spherical inorganic filler having an average primary particle size in the range of 150 nm to 230 nm is used, as described above, the colored light thus obtainable is bluish, and the color tone adaptability to dentine is likely to be poor in a cavity formed over from the enamel to the dentine; however, the curable composition is useful for the restoration of the enamel, and is particularly useful for the restoration of an incisal part.

It is desirable that the spherical inorganic filler (D) is approximately spherical, and it is not necessarily essential that the spherical inorganic filler (D) is a perfect true sphere. It is desirable that the average uniformity described above is 0.6 or higher, and more preferably 0.8 or higher.

Regarding the spherical inorganic filler (D), any filler used as the spherical inorganic filler (b2) that constitutes the organic-inorganic composite filler (B) can be used without limitations. Specific examples include inorganic powders of amorphous silica, silica-titanium group element oxide-based composite oxide particles (silica-zirconia, silica-titania, or the like), quartz, alumina, barium glass, strontium glass, lanthanum glass, fluoroaluminosilicate glass, ytterbium fluoride, zirconia, titania, and colloidal silica.

Among these, from the viewpoint that adjustment of the refractive index of the filler is easy, silica-titanium group element oxide-based composite oxide particles are preferred, similarly to the spherical inorganic filler (b2).

Regarding the silica-titanium group element oxide-based composite oxide particles, examples include silica-titania, silica-zirconia, and silica-titania-zirconia. Among these, from the viewpoint that adjustment of the refractive index of the filler is enabled, and high opacity to X-rays can also be imparted, silica-zirconia is preferred. The composite ratio is not particularly limited; however, from the viewpoint of imparting sufficient opacity to X-rays and adjusting the refractive index to a suitable range that will be described below, it is preferable that the content of silica is 70 mol % to 95 mol %, and the content of the titanium group element oxide is 5 mol % to 30 mol %. In the case of silica-zirconia, the refractive index can be freely changed by changing the respective composite ratios as such.

For these silica-titanium group element oxide-based composite oxide particles, compounding of a metal oxide other than silica and a titanium group element oxide is also allowed as long as the amount is small. Specifically, an alkali metal oxide such as sodium oxide or lithium oxide may be incorporated in an amount of 10 mol % or less.

These silica-titanium group element oxide-based composite oxide particles may be surface-treated with a silane coupling agent, similarly to the spherical inorganic filler (b2). Through a surface treatment using a silane coupling agent, when the curable composition of the present invention is cured, excellent interfacial strength between the composite oxide particles and the cured product portion of the polymerizable monomer (A) is obtained. Representative examples of the silane coupling agent include organosilicon compounds such as γ-methacryloyloxyalkyltrimethoxysilane and hexamethyldisilazane. The amount of surface treatment with these silane coupling agents is not particularly limited, and an optimal value may be decided after the mechanical properties and the like of a cured product of the curable composition thus obtainable are checked in advance by experiments. An example of a suitable range is the range of 0.1 to 15 parts by mass with respect to 100 parts by mass of the spherical inorganic filler (D).

As described above, a colored light induced by interference is exhibited with satisfactory color tone adaptability to natural teeth in the case of satisfying the following formulae (3) and (4):

$$nP < nF_D \quad (3)$$

in which nP represents the refractive index of a polymer of the polymerizable monomer (A) at 25° C.; and $nF_D$ represents the refractive index of the spherical inorganic filler (D) at 25° C., $$nM_{b1} < nF_D \quad (4)$$

in which $nM_{b1}$ represents the refractive index of the organic resin matrix (b1) at 25° C.; and $nF_D$ represents the refractive index of the spherical inorganic filler (D) at 25° C.

That is, the refractive index $nF_D$ of the spherical inorganic filler (D) is in a state of being higher than the refractive index nP of a polymer of the polymerizable monomer (A) and the refractive index $nM_{b1}$ of the organic resin matrix (b1).

In a case in which the curable composition of the present invention is used as a dental curable composition, in order to realize color tone adaptability that enables restoration close to natural teeth, the difference in the refractive index between the refractive index $nF_D$ of the spherical inorganic filler (D) and the refractive index nP of a polymer of the polymerizable monomer (A), and the difference in the refractive index between the refractive index $nF_D$ of the spherical inorganic filler (D) and the refractive index $nM_{b1}$ of the organic resin matrix (b1) are preferably adjusted to 0.001 or greater, and more preferably adjusted to 0.002 or greater.

Furthermore, in a case in which the cured product of the curable composition of the present invention has high transparency, colored light is exhibited more clearly, and satisfactory color tone adaptability is obtained. Therefore, the difference in the refractive index between the refractive index $nF_D$ of the spherical inorganic filler (D) and the refractive index nP of a polymer of the polymerizable monomer component (A), and the difference in the refractive index between the refractive index $nF_D$ of the spherical inorganic filler (D) and the refractive index $nM_{b1}$ of the organic resin matrix (b1) are preferably adjusted to 0.1 or less, and more preferably to 0.05 or less. Thus, it is desirable that transparency is not impaired as far as possible.

In a case in which the curable composition of the present invention includes the spherical inorganic filler (D), the content of the spherical inorganic filler is preferably 50 to 1,500 parts by mass with respect to 100 parts by mass of the polymerizable monomer (A). When the spherical inorganic filler (D) is incorporated in an amount of 50 parts by mass or more, a colored light induced by interference is satisfactorily exhibited. On the other hand, it is difficult in view of operation to incorporate the spherical inorganic filler in an amount of more than 1,500 parts by mass. When the filler is incorporated in an amount in the range of 50 to 1,500 parts by mass, the curable composition exhibits satisfactory operability and is suitable as a material for an operation of filling in a cavity, as in the case of a dental curable composition, particularly a dental filling restorative material. When these are taken into consideration, the content of the spherical inorganic filler (D) is more preferably 100 to 1,500 parts by mass, and even more preferably 150 to 1,500 parts by mass, with respect to 100 parts by mass of the polymerizable monomer (A).

In a case in which only the organic-inorganic composite filler (B) is used as a constituent, as described above, the content of the organic-inorganic composite filler (B) is preferably 50 to 1,000 parts by mass with respect to 100 parts by mass of the polymerizable monomer component (A). In order to obtain satisfactory operability of a paste of the curable composition and satisfactory mechanical strength of the cured product, the content of the organic-inorganic composite filler (B) is more preferably 70 to 600 parts by mass, and even more preferably 100 to 400 parts by mass, with respect to 100 parts by mass of the polymerizable monomer component (A). Furthermore, the percentage content of the spherical inorganic filler (b2) in the organic-inorganic composite filler (B) is preferably 30% to 95% by mass, and more preferably 40% to 90% by mass. Therefore, the amount of incorporation of the spherical inorganic filler that affects exhibition of a colored light induced by interference is more than or equal to 10% by mass ((50/150)× 30%) and less than or equal to 86.4% by mass ((1,000/1,100)×95%) in the curable composition.

In a case in which the organic-inorganic composite filler (B) and the spherical inorganic filler (D) are used in combination, when the inorganic filler components are incorporated in an amount of incorporation of 10% to 86% by mass in the curable composition, a colored light induced by interference is satisfactorily exhibited. The amount of incorporation of the inorganic filler components is more preferably 15% to 86% by mass, and even more preferably 20% to 86% by mass. In order to obtain satisfactory operability of a paste of the curable composition and satisfactory mechanical strength of the cured product, it is preferable that the mixing ratio between the organic-inorganic composite filler (B) and the spherical inorganic filler (D) is adjusted to 10:90 to 90:10, more preferably to 20:80 to 80:20, and even more preferably to 30:70 to 70:30.

Among the spherical inorganic fillers (D), a silica-based filler with which the adjustment of the refractive index is easy, particularly a silica-titanium group oxide-based composite oxide, has a refractive index in the range of about 1.45 to 1.58 according to the content of the silica portion. That is, in a case in which a silica-titanium group element oxide-based composite oxide is used as the spherical inorganic filler (D), when the refractive index of the polymerizable monomer (A) is in the above-mentioned range (in the range of 1.38 to 1.55), the refractive index nP of a polymer obtainable from the polymerizable monomer (A) is approximately in the range of 1.40 to 1.57. Therefore, the spherical inorganic filler (D) can be easily selected so as to satisfy the above-mentioned condition (formula (3)). That is, it is desirable to use a silica-titanium group oxide-based composite oxide (silica-titania, silica-zirconia, or the like) including an adequate amount of silica portion.

Furthermore, regarding the spherical inorganic filler (D), it is preferable to use a spherical inorganic filler having substantially the same average primary particle size and refractive index as the spherical inorganic filler (b2). Thereby, a colored light induced by light interference can be identified clearly. According to the present invention, when it is said to have substantially the same average primary particle size and refractive index, the difference with regard to the average primary particle size is 10 nm or less, and more preferably 5 nm or less, and the difference with regard to the refractive index is 0.01 or less, and more preferably 0.005 or less.

Furthermore, it is preferable that the difference between the filling ratio of the spherical inorganic filler (D) in the curable composition (weight of spherical inorganic filler (D)/(weight of polymerizable monomer (A)+weight of spherical inorganic filler (D))) and the filling ratio of the spherical inorganic filler (b2) in the organic-inorganic composite filler (B) (weight of spherical inorganic filler (b2)/weight of organic-inorganic composite filler (B)) is 0% to 35%, because a colored light induced by light interference can be identified clearly. The difference in the filling ratio is more preferably 0% to 30%, and even more preferably 0% to 25%.

<Other Additives>

In the curable composition of the present invention, other known additives can be incorporated, in addition to the components (A) to (D), to the extent that the effects are not impaired. Specific examples include a polymerization inhibitor and an ultraviolet absorber. Furthermore, for the purpose of viscosity adjustment or the like, a filler having a particle size of less than 0.1 µm, which is sufficiently smaller than the wavelength of light and does not easily affect color tone and transparency, can be incorporated.

In the present invention, as described above, restoration with satisfactory color tone adaptability to natural teeth is enabled with a single paste (curable composition), even without using coloring materials such as a pigment. Therefore, an embodiment in which a pigment having a risk of causing discoloration over time is not incorporated is preferred. However, according to the present invention, it is not intended to deny incorporation of a pigment per se, and a pigment may be incorporated to the extent that does not hamper a colored light induced by interference of spherical fillers. Specifically, a pigment may be incorporated in an amount of about 0.0005 to 0.5 parts by mass, and preferably about 0.001 to 0.3 parts by mass, with respect to 100 parts by mass of the polymerizable monomer (A).

The curable composition of the present invention is suitably used as a dental curable composition as described above, particularly as a dental filling restorative material that is represented by a photocurable composite resin. However, the use is not limited thereto, and the curable composition can also be suitably used in other use applications. Examples of the other use applications include dental cement and a restorative material for abutment construction.

EXAMPLES

Hereinafter, the present invention will be described more specifically by way of Examples; however, the present invention is not intended to be limited to these Examples.

The methods for measuring various physical properties according to the present invention are respectively as follows.

(1) Average Primary Particle Size

A photograph of a powder was taken with a scanning electron microscope ("XL-30S", manufactured by Philips N.V.) at a magnification ratio of 5,000 to 100,000 times, and the image thus taken was processed using an image analysis software program ("IP-1000PC", manufactured by Asahi Kasei Engineering Corp.). The number (30 or more) and the particle sizes (maximum diameters) of particles observed within a unit viewing field of that photograph were measured, and the average primary particle size was calculated by the following formula based on the measured values.

$$\overline{x} = \frac{\sum_{i=1}^{n} x_i}{n} \text{ (Number average)}$$

($n$ : number of particles, $x_i$ : primary particle size (maximum diameter) of $i$-th particle)

(2) Abundance Proportion of Average Particle-Sized Particles

The number of particles having a particle size within the range of 5% greater or less than the average primary particle size obtained in the above section (1) was measured, and this number was divided by the number of particles (30 or more) observed within a unit viewing field of the photograph. The value thus obtained was subtracted from 1, and the resultant was multiplied by 100. Thus, the proportion of particles that are present in the range of 5% greater or less than the average primary particle size was calculated, and this was designated as the abundance proportion of the average particle-sized particles.

(3) Average Uniformity

A photograph of a powder was taken with a scanning electron microscope, and for the particles observed within a unit viewing field of the photograph, the number (n: 30 or more), the maximum diameter of each particle as the major axis (Li), and the diameter in a direction orthogonally intersecting the major axis as the minor axis (Bi) were determined. Thus, the average uniformity was calculated by the following formula.

$$\text{Average uniformity} = \frac{\sum_{i=1}^{n} Bi/Li}{n}$$

(4) Average Particle Size (Particle Size) of Organic-Inorganic Composite Filler 0.1 g of an organic-inorganic composite filler was dispersed in 10 mL of ethanol, and the dispersion was irradiated with ultrasonic waves for 20 minutes. The median diameter of volume statistics was determined by applying an optical model "Fraunhofer" using a particle size distribution meter ("LS230", manufactured by Beckman Coulter, Inc.) according to a laser diffraction-scattering method.

(5) Measurement of Refractive Index

<Refractive Index of Polymerizable Monomer Component (A)>

The refractive index of a polymerizable monomer (or a mixture of polymerizable monomers) used was measured in a constant temperature chamber at 25° C. using an Abbe refractometer (manufactured by Atago Co., Ltd.).

<Refractive Index (nP) of Polymer of Polymerizable Monomer Component (A)>

The refractive index of a polymer of polymerizable monomers (or a mixture of polymerizable monomers) used was measured using a polymer polymerized under conditions almost the same as the polymerization conditions in a cavity, in a constant temperature chamber at 25° C. using an Abbe refractometer (manufactured by Atago Co., Ltd.).

That is, a uniform polymerizable monomer (or a mixture of polymerizable monomers) obtained by mixing 0.2% by mass of camphor-quinone, 0.3% by mass of ethyl N,N-dimethyl-p-benzoate, and 0.15% by mass of hydroquinone monomethyl ether was introduced into a mold having a hole having a size of 7 mm$\phi$×0.5 mm, and a polyester film was pressure-welded on both surfaces. Subsequently, the polymerizable monomer was cured by irradiating the monomer with light for 30 seconds using a halogen type dental light irradiator ("Demetron LC", manufactured by Sybron Dental Specialties, Inc.) at a quantity of light of 500 mW/cm$^2$, and then the cured product was removed from the mold. Thus, a polymer of the polymerizable monomer was produced. When the polymer was placed in an Abbe refractometer (manufactured by Atago Co., Ltd.), for the purpose of tightly adhering the polymer with the measuring surface, the sample was not dissolved, but a solvent having a refractive index higher than that of the sample (bromonaphthalene) was added dropwise to the sample, and the refractive index was measured.

<Refractive Index $nM_{b1}$ of Organic Resin Matrix (b1)>

The refractive index of the organic resin matrix was measured in a constant temperature chamber at 25° C. using a polymer obtained by polymerizing under almost the same conditions as the polymerization conditions at the time of producing the organic-inorganic composite filler, using an Abbe refractometer (manufactured by Atago Co., Ltd.).

That is, a uniform polymerizable monomer (or a mixture of polymerizable monomers) mixed with 0.5% by mass of azobisisobutyronitrile was introduced into a mold having a hole having a size of 7 mm$\phi$×0.5 mm, and a polyester film was pressure-welded on both surfaces. Subsequently, the polymerizable monomer was heated for one hour under an added pressure of nitrogen and was polymerized and cured. Subsequently, the resultant was removed from the mold, and thus a polymer of the polymerizable monomer (organic resin matrix) was produced. When the polymer is placed in an Abbe refractometer (manufactured by Atago Co., Ltd.), for the purpose of tightly adhering the polymer with the measuring surface, the sample was not dissolved, but a solvent having a higher refractive index than the sample (bromonaphthalene) was added dropwise to the sample, and the refractive index was measured.

<Refractive Indices of Spherical Inorganic Filler (b2), Spherical Inorganic Filler (D), and Irregularly Shaped Inorganic Filler>

The refractive indices of spherical inorganic fillers and irregularly shaped inorganic filler used were measured according to a liquid immersion method using an Abbe refractometer (manufactured by Atago Co., Ltd.).

That is, in a constant temperature chamber at 25° C., in a 100-mL sample bottle, 1 g of a spherical inorganic filler, an irregularly shaped inorganic filler, or a surface-treated product thereof was dispersed in 50 mL of anhydrous toluene. While this dispersion liquid was stirred with a stirrer, 1-bromotoluene was added dropwise in small amounts, the refractive index of the dispersion liquid at the time point when the dispersion liquid became most transparent was measured, and the value thus obtained was designated as the refractive index of the inorganic filler.

(6) Evaluation of Colored Light by Visual Inspection

A paste of each of the curable compositions produced in Examples and Comparative Examples was introduced into a mold having a hole having a size of 7 mm$\phi$×1 mm, and a polyester film was pressure-welded on both surfaces. Both surfaces were cured by irradiating with light for 30 seconds with a visible light irradiator (POWER LIGHT, manufactured by Tokuyama Corp.), and then the resultant was removed from the mold. The cured product was mounted on an adhesive surface of a black tape (carbon tape) that measured about 10 mm on each edge, and the color tone of colored light was checked by visual inspection.

(7) Wavelength of Colored Light

A paste of each of the curable compositions produced in Examples and Comparative Examples was introduced into a mold having a hole having a size of 7 mm$\phi$×1 mm, and a polyester film was pressure-welded on both surfaces. Both surfaces were cured by irradiating with light for 30 seconds with a visible light irradiator (POWER LIGHT, manufactured by Tokuyama Corp.), and then the resultant was removed from the mold. The spectral reflectance was measured using a color difference meter ("TC-1800 MKII", manufactured by Tokyo Denshoku Co., Ltd.) on the black background color (backing having a value of 1 according to the Munsell Color System) and on the white background color (backing having a value of 9.5 according to the Munsell Color System), and the maximum point of the reflectance on the black background color was designated as the wavelength of the colored light.

(8) Evaluation of Color Tone Adaptability

A hard resin tooth that reproduced an incisal part loss cavity (width 2 mm, depth 1 mm) of the upper right No. 1, a hard resin tooth that reproduced a Class I cavity (diameter 4 mm, depth 2 mm) of the lower right No. 6, or a hard resin tooth that reproduced a tooth cervix loss cavity (diameter 4 mm, depth 2 mm) of upper right No. 3 was used. The cavity was filled with a curable paste, the paste was polished after curing, and the color tone adaptability was checked by visual inspection. The evaluation criteria are shown below. Furthermore, for the hard resin teeth, a hard resin tooth of high chroma (corresponding to A4) and a hard resin tooth of low chroma (corresponding to A1) in the class of A system (red-brown) according to Shade Guide "VITAPAN Classical", and a hard resin tooth of high chroma (corresponding to B4) and a hard resin tooth of low chroma (corresponding to B1) in the class of B system (red-yellow) according to Shade Guide "VITAPAN Classical" were used.

—Evaluation Criteria—

5: The color tone of the restoration product is indistinguishable from that of the hard resin tooth.

4: The color tone of the restoration product highly matches with that of the hard resin tooth.

3: The color tone of the restoration product is similar to that of the hard resin tooth.

2: The color tone of the restoration product is similar to that of the hard resin tooth; however, adaptability is not satisfactory.

1: The color tone of the restoration product does not match with that of the hard resin tooth.

(9) Change in Color Tone Over Time

A paste of each of the curable compositions produced in Examples and Comparative Examples was introduced into a mold having a hole having a size of 7 mmϕ×1 mm, and a polyester film was pressure-welded on both surfaces. Both surfaces were cured by irradiating with light for 30 seconds with a visible light irradiator (POWER LIGHT, manufactured by Tokuyama Corp.), and then the resultant was removed from the mold. The cured product was stored in water at 37° C. for 4 months, and the color tone was measured using a color difference meter ("TC-1800 MKII", manufactured by Tokyo Denshoku Co., Ltd.). The difference between the color tones before and after the storage is represented by ΔE* in the CIELab, according to the following formula.

$$\Delta E^* = \{(\Delta L^*)^2 + (\Delta a^*)^2 + (\Delta b^*)^2\}^{1/2}$$

$\Delta L^* = L1^* - L2^*$
$\Delta a^* = a1^* - a2^*$
$\Delta b^* = b1^* - b2^*$ in which, $L1^*$: psychometric lightness index of cured product after storage, $a1^*$ and $b1^*$: psychometric chroma coordinates of cured product after storage, $L2^*$: psychometric lightness index of cured product before storage, $a2^*$ and $b2^*$: psychometric chroma coordinates of cured product before storage, $\Delta E^*$: amount of change in color tone.

The polymerizable monomers, polymerization initiators, and the like used in Examples and Comparative Examples were as follows.

[Polymerizable Monomer]
  1,6-Bis(methacrylethyloxycarbonylamino)trimethylhexane (hereinafter, abbreviated to "UDMA")
  Triethylene glycol dimethacrylate (hereinafter, abbreviated to "3G")
  2,2-Bis[(3-methacryloyloxy-2-hydroxypropyloxy)phenyl]propane (hereinafter, abbreviated to "bis-GMA")
[Polymerization Initiator]
  Camphor-quinone (hereinafter, abbreviated to "CQ")
  Ethyl N,N-dimethyl-p-benzoate (hereinafter, abbreviated to "DMBE")
  Azobisisobutyronitrile (hereinafter, abbreviated to "AIBN")
[Polymerization Inhibitor]
  Hydroquinone monomethyl ether (hereinafter, abbreviated to "HQME")
[Colorant]
  Titanium dioxide (white pigment)
  Pigment Yellow (yellow pigment)
  Pigment Red (red pigment)
  Pigment Blue (blue pigment)

[Production of Mixture of Polymerizable Monomers]

The polymerizable monomers shown in Table 1 were mixed, and polymerizable monomers M1, M2, M3, and M4 were produced. The values in the parentheses in Table 1 represent the mass ratios of the respective polymerizable monomers.

TABLE 1

| | | Refractive index | |
|---|---|---|---|
| | Polymerizable monomer | Before curing | After curing |
| M1 | UDMA(60)/3G(40) | 1.474 | 1.509 |
| M2 | bis-GMA(50)/3G(50) | 1.506 | 1.540 |
| M3 | bis-GMA(1)/3G(40)/UDMA(59) | 1.474 | 1.510 |
| M4 | bis-GMA(8)/3G(40)/UDMA(52) | 1.479 | 1.514 |

[Production of Spherical Inorganic Filler and Irregularly Shaped Inorganic Filler]

A spherical inorganic filler was produced by the method described in Japanese Unexamined Patent Application, Publication No. S58-110414, Japanese Unexamined Patent Application, Publication No. S58-156524, and the like. That is, a spherical inorganic filler was produced using a so-called sol-gel method of adding a mixed solution including a hydrolyzable organosilicon compound (tetraethyl silicate or the like) and a hydrolyzable organic titanium group metal compound (tetrabutyl zirconate, tetrabutyl titanate, or the like) into an ammoniacal alcohol (for example, methanol, ethanol, isopropyl alcohol, or isobutyl alcohol) solution having aqueous ammonia incorporated therein, performing hydrolysis, and precipitating out a reaction product.

An irregularly shaped inorganic filler was produced by the method described in Japanese Unexamined Patent Application, Publication No. H02-132102, Japanese Unexamined Patent Application, Publication No. H03-197311, or the like. That is, an irregularly shaped inorganic filler was produced using a method of dissolving an alkoxysilane compound in organic solvent, adding water to this solution to perform partial hydrolysis, further adding thereto an alkoxide of another metal and an alkali metal compound to be compounded, thereby performing hydrolysis to produce a gel-like material, subsequently drying the gel-like material, subsequently pulverizing the dried product as necessary, and calcining the pulverization product.

The spherical inorganic fillers and irregularly shaped inorganic fillers used in Examples are shown in Table 2.

TABLE 2

| | Composition and shape of filler | | Average particle size nm | Refractive index | Abundance proportion of average particle-sized particles[1] % | Average uniformity |
|---|---|---|---|---|---|---|
| | Composition (mol %) | Shape | | | | |
| PF1 | SiO$_2$/ZrO$_2$/Na$_2$O = 89.8/9.0/1.2 | Spherical | 178 | 1.515 | 91 | 0.98 |
| PF2 | SiO$_2$/ZrO$_2$/Na$_2$O = 89.8/9.0/1.2 | Spherical | 230 | 1.515 | 92 | 0.97 |
| PF3 | SiO$_2$/ZrO$_2$/Na$_2$O = 89.8/9.0/1.2 | Spherical | 281 | 1.515 | 94 | 0.96 |
| PF4 | SiO$_2$/ZrO$_2$/Na$_2$O = 89.8/9.0/1.2 | Spherical | 80 | 1.515 | 92 | 0.94 |

TABLE 2-continued

| | Composition and shape of filler | | Average particle size nm | Refractive index | Abundance proportion of average particle-sized particles[1] % | Average uniformity |
|---|---|---|---|---|---|---|
| | Composition (mol %) | Shape | | | | |
| PF5 | $SiO_2/ZrO_2/Na_2O$ = 89.8/9.0/1.2 | Spherical | 280 | 1.515 | 87 | 0.94 |
| PF6 | $SiO_2/ZrO_2/Na_2O$ = 88.7/10.8/1.2 | Spherical | 282 | 1.522 | 93 | 0.92 |
| PF7 | $SiO_2/ZrO_2/Na_2O$ = 83.9/14.3/1.8 | Spherical | 286 | 1.542 | 91 | 0.90 |
| PF8 | $SiO_2/TiO_2/Na_2O$ = 90.1/9.4/1.2 | Spherical | 280 | 1.522 | 95 | 0.95 |
| PF9 | $SiO_2/TiO_2/Na_2O$ = 90.6/7.5/1.8 | Spherical | 281 | 1.515 | 90 | 0.96 |
| PF10 | $SiO_2/ZrO_2/Na_2O$ = 88.7/10.8/1.2 | Spherical | 340 | 1.522 | 91 | 0.93 |
| PF11 | $SiO_2/ZrO_2/Na_2O$ = 88.7/10.8/1.2 | Spherical | 260 | 1.522 | 93 | 0.94 |
| PF12 | $SiO_2/ZrO_2/Na_2O$ = 89.8/9.0/1.2 | Irregularly shaped | 500 | 1.515 | 50 | — |

[1]The abundance proportion of average particle-sized particles is the proportion (%) of particles that are present in the range of 5% greater or less than the average particle size.

[Production of Irregularly Shaped Organic-Inorganic Composite Filler]

0.5% by mass of a thermal polymerization initiator (AIBN) was dissolved in advance in the polymerizable monomers shown in Table 1, a predetermined amount (Table 3) of an inorganic filler was added and mixed with the solution, and the resultant was made into a paste with a mortar. This paste was heated for one hour under an added pressure of nitrogen at 95° C., and thereby the paste was polymerized and cured. This cured product was pulverized using a vibratory ball mill, and was further surface-treated by heating to reflux for 5 hours at 90° C. in ethanol using 0.02% by mass of γ-methacryloyloxypropyltrimethoxysilane. Thus, irregularly shaped organic-inorganic composite fillers CF1 to CF16 as shown in the following Table 3 were obtained. The values in the parentheses in Table 3 represent the amounts of use (unit: parts by mass) of the polymerizable monomers and inorganic fillers.

TABLE 3

| | Polymerizable monomer | Inorganic filler | Filler filling ratio | Average particle size (μm) |
|---|---|---|---|---|
| CF1 | M1 (100) | PF1 (300) | 75 | 30 |
| CF2 | M1 (100) | PF2 (300) | 75 | 28 |
| CF3 | M1 (100) | PF3 (300) | 75 | 23 |
| CF4 | M1 (100) | PF4 (300) | 75 | 24 |
| CF5 | M1 (100) | PF5 (300) | 75 | 29 |
| CF6 | M1 (100) | PF6 (300) | 75 | 26 |
| CF7 | M2 (100) | PF7 (300) | 75 | 25 |
| CF8 | M1 (100) | PF8 (300) | 75 | 24 |
| CF9 | M1 (100) | PF12 (300) | 75 | 28 |
| CF10 | M1 (100) | PF3 (233) | 70 | 28 |
| CF11 | M1 (100) | PF3 (150) | 60 | 33 |
| CF12 | M1 (100) | PF3 (400) | 80 | 31 |
| CF13 | M4 (100) | PF6 (150) | 75 | 28 |
| CF14 | M2 (100) | PF6 (150) | 75 | 28 |
| CF15 | M1 (100) | PF10 (300) | 75 | 28 |
| CF16 | M1 (100) | PF11 (300) | 75 | 28 |

[Production of Approximately Spherical-Shaped Organic-Inorganic Composite Filler (CF17)]

100 g of a spherical inorganic filler (PF3) was added to 200 g of water, and an aqueous dispersion of these was obtained using a circulation type pulverizer SC MILL (manufactured by Nippon Coke & Engineering Co., Ltd.).

On the other hand, 4 g (0.016 mol) of γ-methacryloyloxypropyltrimethoxysilane and 0.003 g of acetic acid were added to 80 g of water, and the mixture was stirred for 1 hour and 30 minutes. Thus, a uniform solution at pH 4 was obtained. This solution was added to the spherical inorganic filler dispersion liquid, and the mixture was mixed until the dispersion liquid became uniform. Subsequently, while the dispersion liquid was lightly mixed, the dispersion liquid was supplied onto a disc rotating at high speed and was granulated by a spray drying method.

Spray drying was carried out using a spray dryer TSR-2W (manufactured by Sakamoto Giken Co., Ltd.) that includes a rotating disc and sprays by means of centrifugal force. The speed of rotation of the disc was 10,000 rpm, and the temperature of air in a dry atmosphere was 200° C. Subsequently, a powder obtained by being granulated by spraying and drying was dried in a vacuum at 60° C. for 18 hours, and 73 g of approximately spherically shaped aggregates were obtained.

Next, 10 g of the aggregates were immersed in a polymerizable monomer solution (including 36 parts by mass of a polymerizable monomer with respect to 100 parts by mass of an organic solvent) obtained by mixing 1.8 g of polymerizable monomer M1, 0.005 g of AIBN as a thermal polymerization initiator, and 5.0 g of methanol as an organic solvent. The mixture was sufficiently stirred, it was checked that this mixture was brought to a slurry state, and then the slurry was left to stand for one hour.

The above-described mixture was transferred into a rotary evaporator. In a stirred state, the mixture was dried for one hour under the conditions of a degree of pressure reduction of 10 hPa and a heating condition of 40° C. (a warm water bath was used), and the organic solvent was removed. When the organic solvent was removed, a powder having high fluidity was obtained.

While the powder thus obtained was stirred in a rotary evaporator, the powder was heated for one hour under the conditions of a degree of pressure reduction of 10 hPa and a heating condition of 100° C. (an oil bath was used), and thereby the polymerizable monomer in the powder was polymerized and cured. Through this operation, 9 g of an approximately spherical-shaped organic-inorganic composite filler (CF17), in which the surface of spherically shaped aggregates was coated with an organic polymer, was obtained. The average particle size of this organic-inorganic composite filler was 33 µm.

Examples 1 to 22

0.3% by mass of CQ, 1.0% by weight of DMBE, and 0.15% by mass of HQME were added to the polymerizable monomers M1, M2, M3, or M4, and the components were mixed. Thus, uniform polymerizable monomer compositions were produced. Next, each of the fillers shown in Table 2 and Table 3 was weighed in a mortar, each of the above-mentioned polymerizable monomers was slowly added thereto under red light, and the mixture was sufficiently kneaded in the dark to obtain a uniform curable paste. This paste was further degassed under reduced pressure to eliminate air bubbles, and thus a curable composition was produced. For the curable composition thus obtained, various physical properties were evaluated based on the above-described methods. The compositions and results are shown in Table 4 and Table 5. The values in the parentheses in Table 4 represent the amounts of use (unit: parts by mass) of the polymerizable monomer (A), the organic-inorganic composite filler (B), and the spherical inorganic filler (D), and the symbol "-" represents that the component is not used.

Comparative Examples 1 to 6, 8, 9

0.3% by mass of CQ, 1.0% by mass of DMBE, and 0.15% by mass of HQME were added to the polymerizable monomer M1 or M2, the components were mixed, and thus uniform polymerizable monomer compositions were produced. Next, each of the various fillers shown in Table 2 and Table 3 was weighed in a mortar, each of the above-mentioned polymerizable monomers was slowly added thereto under red light, and the mixture was sufficiently kneaded in the dark to obtain a uniform curable paste. This paste was further degassed under reduced pressure to eliminate air bubbles, and thus a curable composition was produced. For the curable composition thus obtained, various physical properties were evaluated based on the above-described methods. The compositions and results are shown in Table 4 and Table 5.

Comparative Example 7

0.3% by mass of CQ, 1.0% by mass of DMBE, and 0.15% by mass of HQME were added to the polymerizable monomer M1, and the components were mixed. Thus, a uniform polymerizable monomer composition was produced. Next, the organic-inorganic composite filler shown in Table 3 was weighed in a mortar, and the above-mentioned polymerizable monomer was slowly added thereto under red light. Furthermore, 0.040 g of titanium dioxide (white pigment), 0.0008 g of Pigment Yellow (yellow pigment), 0.0004 g of Pigment Red (red pigment), and 0.0002 g of Pigment Blue (blue pigment) were added to the mixture, and the mixture was sufficiently kneaded in the dark to obtain a uniform curable paste. Furthermore, this paste was degassed under reduced pressure to eliminate air bubbles, and pigments were added in the composition shown in Comparative Example 1. Thus, a curable composition adjusted to a color tone (corresponding to A4) that matched with A system of high chroma hard resin teeth was produced. Through an evaluation by visual inspection, a color tone (corresponding to A4) that matched with A system of high chroma hard resin teeth was obtained. Subsequently, various physical properties were evaluated based on the above-described method. The composition and results are shown in Table 4 and Table 5.

TABLE 4

| | Polymerizable monomer (A) | Organic-inorganic composite filler (B) | Spherical inorganic filler (D) | Difference in refractive index[1] | Visual inspection of colored light | Colored light wavelength (nm) On black background | Colored light wavelength (nm) On white background | Change in color tone over time ΔE* |
|---|---|---|---|---|---|---|---|---|
| Example 1 | M1 (100) | CF2 (400) | — | 0 | Yellow | 607 | No maximum | 2.2 |
| Example 2 | M1 (100) | CF3 (400) | — | 0 | Red | 748 | No maximum | 1.7 |
| Example 3 | M1 (100) | CF6 (400) | — | 0 | Red | 756 | No maximum | 1.6 |
| Example 4 | M1 (100) | CF6 (400) | — | 0 | Red | 756 | No maximum | 1.6 |
| Example 5 | M1 (100) | CF6 (400) | — | 0 | Red | 756 | No maximum | 1.6 |
| Example 6 | M2 (100) | CF7 (400) | — | 0 | Red | 748 | No maximum | 1.8 |
| Example 7 | M1 (100) | CF8 (400) | — | 0 | Red | 751 | No maximum | 1.9 |
| Example 8 | M3 (100) | CF3 (400) | — | −0.001 | Red | 746 | No maximum | 1.8 |
| Example 9 | M4 (100) | CF3 (400) | — | −0.005 | Red | 758 | No maximum | 1.9 |
| Example 10 | M1 (100) | CF2 (240) | PF2 (160) | 0 | Yellow | 612 | No maximum | 1.4 |
| Example 11 | M1 (100) | CF3 (240) | PF3 (160) | 0 | Red | 759 | No maximum | 1.6 |
| Example 12 | M1 (100) | CF3 (240) | PF9 (160) | 0 | Red | 754 | No maximum | 1.7 |
| Example 13 | M1 (100) | CF3 (100) | PF3 (300) | 0 | Red | 752 | No maximum | 1.5 |
| Example 14 | M1 (100) | CF10 (167) | PF3 (233) | 0 | Red | 754 | No maximum | 1.8 |
| Example 15 | M1 (100) | CF11 (250) | PF3 (150) | 0 | Red | 756 | No maximum | 1.6 |
| Example 16 | M1 (100) | CF12 (250) | FF3 (167) | 0 | Red | 757 | No maximum | 1.4 |
| Example 17 | M4 (100) | CF13 (250) | PF6 (167) | 0 | Red | 751 | No maximum | 1.3 |
| Example 18 | M1 (100) | CF17 (400) | — | 0 | Red | 750 | No maximum | 1.2 |
| Example 19 | M1 (100) | CF15 (400) | — | 0 | Red | 741 | No maximum | 1.3 |
| Example 20 | M1 (100) | CF16 (400) | — | 0 | Red | 668 | No maximum | 1.2 |
| Example 21 | M1 (100) | CF17 (240) | PF3 (160) | 0 | Red | 748 | No maximum | 1.3 |
| Example 22 | M1 (100) | CF17 (300) | PF3 (100) | 0 | Red | 743 | No maximum | 1.3 |

[1]Refractive index of organic resin matrix − refractive index after curing of polymerizable monomer

|  | Polymerizable monomer (A) | Organic-inorganic composite filler (B) | Spherical inorganic filler (D) | Difference in refractive index[1] | Visual inspection of colored light | Colored light wavelength (nm) On black background | Colored light wavelength (nm) On white background | Change in color tone over time ΔE* |
|---|---|---|---|---|---|---|---|---|
| Comparative Example 1 | M1 (100) | CF4 (400) | — | 0 | None | 403 | No maximum | 1.8 |
| Comparative Example 2 | M1 (100) | CF5 (400) | — | 0 | Pale red | 739 | No maximum | 2.3 |
| Comparative Example 3 | M1 (100) | CF9 (400) | — | 0 | None | No maximum | No maximum | 2.4 |
| Comparative Example 4 | M2 (100) | CF14 (400) | — | 0 | Blue | 475 | No maximum | 2.1 |
| Comparative Example 5 | M1 (100) | CF4 (240) | PF4 (160) | 0 | None | 411 | No maximum | 2.0 |
| Comparative Example 6 | M1 (100) | CF5 (240) | PF5 (160) | 0 | Pale red | 745 | No maximum | 1.8 |
| Comparative Example 7 | M1 (100) | CF4 (400) | — | 0 | — | — | — | 4.8 |
| Comparative Example 8 | M1 (100) | CF1 (400) | — | 0 | Blue | 480 | No maximum | 1.7 |
| Comparative Example 9 | M1 (100) | CF1 (400) | — | 0 | Blue | 480 | No maximum | 1.7 |

[1] Refractive index of organic resin matrix − refractive index after curing of polymerizable monomer

TABLE 5

|  |  |  | Color tone adaptability | | | |
|---|---|---|---|---|---|---|
|  | Hard resin | | A system | | B system | |
|  | tooth | Filling site | (Low chroma) | (High chroma) | (Low chroma) | (High chroma) |
| Example 1 | Lower right No. 6 | Central part of occlusal surface | 3 | 3 | 4 | 4 |
| Example 2 | Lower right No. 6 | Central part of occlusal surface | 4 | 4 | 4 | 3 |
| Example 3 | Lower right No. 6 | Central part of occlusal surface | 4 | 4 | 4 | 3 |
| Example 4 | Upper right No. 3 | Tooth cervix | 4 | 4 | 4 | 4 |
| Example 5 | Upper right No. 1 | Incisal part | 4 | 4 | 4 | 4 |
| Example 6 | Lower right No. 6 | Central part of occlusal surface | 4 | 4 | 4 | 3 |
| Example 7 | Lower right No. 6 | Central part of occlusal surface | 4 | 4 | 4 | 3 |
| Example 8 | Lower right No. 6 | Central part of occlusal surface | 4 | 4 | 4 | 4 |
| Example 9 | Lower right No. 6 | Central part of occlusal surface | 5 | 4 | 4 | 4 |
| Example 10 | Lower right No. 6 | Central part of occlusal surface | 4 | 3 | 4 | 4 |
| Example 11 | Lower right No. 6 | Central part of occlusal surface | 5 | 5 | 5 | 5 |
| Example 12 | Lower right No. 6 | Central part of occlusal surface | 5 | 5 | 5 | 5 |
| Example 13 | Lower right No. 6 | Central part of occlusal surface | 5 | 5 | 5 | 5 |
| Example 14 | Lower right No. 6 | Central part of occlusal surface | 5 | 5 | 5 | 5 |
| Example 15 | Lower right No. 6 | Central part of occlusal surface | 5 | 5 | 5 | 5 |
| Example 16 | Lower right No. 6 | Central part of occlusal surface | 5 | 5 | 5 | 5 |
| Example 17 | Lower right No. 6 | Central part of occlusal surface | 5 | 5 | 5 | 5 |
| Example 18 | Lower right No. 6 | Central part of occlusal surface | 4 | 4 | 4 | 3 |
| Example 19 | Lower right No. 6 | Central part of occlusal surface | 4 | 4 | 4 | 3 |
| Example 20 | Lower right No. 6 | Central part of occlusal surface | 4 | 4 | 4 | 3 |
| Example 21 | Lower right No. 6 | Central part of occlusal surface | 5 | 5 | 5 | 5 |
| Example 22 | Lower right No. 6 | Central part of occlusal surface | 5 | 5 | 5 | 4 |

TABLE 5-continued

|  | Hard resin tooth | Filling site | Color tone adaptability | | | |
|---|---|---|---|---|---|---|
|  |  |  | A system | | B system | |
|  |  |  | (Low chroma) | (High chroma) | (Low chroma) | (High chroma) |
| Comparative Example 1 | Lower right No. 6 | Central part of occlusal surface | 1 | 1 | 1 | 1 |
| Comparative Example 2 | Lower right No. 6 | Central part of occlusal surface | 2 | 2 | 2 | 2 |
| Comparative Example 3 | Lower right No. 6 | Central part of occlusal surface | 1 | 1 | 1 | 1 |
| Comparative Example 4 | Lower right No. 6 | Central part of occlusal surface | 1 | 1 | 2 | 2 |
| Comparative Example 5 | Lower right No. 6 | Central part of occlusal surface | 1 | 1 | 1 | 1 |
| Comparative Example 6 | Lower right No. 6 | Central part of occlusal surface | 2 | 3 | 2 | 2 |
| Comparative Example 7 | Lower right No. 6 | Central part of occlusal surface | 2 | 3 | 1 | 1 |
| Comparative Example 8 | Upper right No. 1 | Incisal part | 4 | 4 | 4 | 4 |
| Comparative Example 9 | Lower right No. 6 | Central part of occlusal surface | 1 | 1 | 2 | 2 |

As is understood from the results of Examples 1 to 22, it can be seen that when the conditions defined in the present invention are satisfied, the dental filling restorative material exhibits a colored light on a black background and has satisfactory color tone adaptability, and a cured product thus obtainable undergoes a small change in the color tone over time.

As is understood from the results of Comparative Examples 1 to 6, it can be seen that when the conditions defined in the present invention are not satisfied, the dental filling restorative material does not exhibit a colored light on a black background (Comparative Examples 1 and 5: average primary particle size of the spherical inorganic filler is 80 nm, Comparative Example 3: the shape of the filler is irregular) or exhibits a weak colored light (Comparative Examples 2 and 6: the amount of presence of the average particle size of the spherical inorganic filler is 87%), or a desired color tone is not obtained after curing and polishing (Comparative Example 4: the condition $nM_{b1} < nF_{b2}$ is not satisfied), and the color tone adaptability is inferior.

As is understood from the results of Comparative Example 7, with regard to a dental filling restorative material for which the color tone was adjusted to a color tone that matched A system of high chroma hard resin teeth by adding pigments to the composition shown in Comparative Example 1, the spectral reflectance was measured on a black background and a white background using a color difference meter ("TC-1800 MKII", manufactured by Tokyo Denshoku Co., Ltd.), and it was observed that the spectral reflection characteristics corresponding to the pigments added are exhibits both on the black background and the white background. The color tone adaptability to a color tone that matched with A system of high chroma hard resin teeth (corresponding to A4) was satisfactory; however, the color tone adaptability to other model teeth was low. Furthermore, the change in the color tone over time was large.

As is understood from the results of Comparative Examples 8 and 9, in a case in which a spherical filler having an average primary particle size of less than 230 nm was used, it can be seen that the colored light was bluish, and in a cavity formed over from the enamel to the dentine, the color tone adaptability to dentine is inferior.

The invention claimed is:

1. A curable composition comprising a polymerizable monomer (A), an organic-inorganic composite filler (B), and a polymerization initiator (C),
    wherein the organic-inorganic composite filler (B) comprises an organic resin matrix (b1) and a spherical inorganic filler (b2) having an average primary particle size of 230 nm to 1,000 nm, 90% or more of the number of individual particles constituting the spherical inorganic filler (b2) are present in a range of 5% greater or less than the average primary particle size, and the following formulae (1) and (2) are satisfied:

$$nP < nF_{b2} \tag{1}$$

wherein nP represents the refractive index of a polymer of the polymerizable monomer (A) at 25° C.; and $nF_{b2}$ represents the refractive index of the spherical inorganic filler (b2) at 25° C., $$nM_{b1} < nF_{b2} \tag{2}$$

wherein $nM_{b1}$ represents the refractive index of the organic resin matrix (b1) at 25° C.; and $nF_{b2}$ represents the refractive index of the spherical inorganic filler (b2) at 25° C.; and
    wherein when a spectral reflectance of a cured product having a thickness of 1 mm of the curable composition is measured using a color difference meter on a black background, the maximum point of the reflectance has a wavelength (peak wavelength) of 550 nm to 770 nm.

2. The curable composition according to claim 1, wherein the difference between the refractive index nP of a polymer of the polymerizable monomer (A) at 25° C. and the refractive index $nM_{b1}$ of the organic resin matrix (b1) at 25° C. is 0.005 or less.

3. The curable composition according to claim 2, wherein the difference between the refractive index nP of a polymer of the polymerizable monomer (A) at 25° C. and the refractive index $nM_{b1}$ of the organic resin matrix (b1) at 25° C. is 0.001 to 0.005.

4. The curable composition according to claim 1, wherein the curable composition further comprises a spherical inorganic filler (D) having an average primary particle size of 230 nm to 1,000 nm, 90% or more of the number of individual particles constituting the spherical inorganic filler (D) are present in the range of 5% greater or less than the average primary particle size, and the following formulae (3) and (4) are satisfied:

$$nP < nF_D \quad (3)$$

wherein nP represents the refractive index of a polymer of the polymerizable monomer (A) at 25° C.; and $nF_D$ represents the refractive index of the spherical inorganic filler (D) at 25° C., $$nM_{b1} < nF_D \quad (4)$$

wherein $nM_{b1}$ represents the refractive index of the organic resin matrix (b1) at 25° C.; and $nF_D$ represents the refractive index of the spherical inorganic filler (D) at 25° C.

5. The curable composition according to claim 4, wherein the difference between the filling ratio of the spherical inorganic filler (D) (weight of spherical inorganic filler (D)/(weight of polymerizable monomer (A)+weight of spherical inorganic filler (D))) and the filling ratio of the spherical inorganic filler (b2) in the organic-inorganic composite filler (B) (weight of spherical inorganic filler (b2)/weight of organic-inorganic composite filler (B)) is 0% to 35%.

6. The curable composition according to claim 1, wherein the polymerizable monomer (A) comprises a (meth)acrylic compound, and the refractive index of the polymerizable monomer (A) at 25° C. is in the range of 1.38 to 1.55.

7. The curable composition according to claim 4, wherein the spherical inorganic filler (b2) and the spherical inorganic filler (D) have substantially the same average primary particle size and substantially the same refractive index.

8. The curable composition according to claim 4, wherein the spherical inorganic filler (b2) and/or the spherical inorganic filler (D) is spherical silica-titanium group element oxide-based composite oxide particles, and the refractive index (25° C.) thereof is in the range of 1.45 to 1.58.

9. A curable composition comprising a polymerizable monomer (A), an organic-inorganic composite filler (B), and a polymerization initiator (C),
wherein the organic-inorganic composite filler (B) comprises an organic resin matrix (b1) and a spherical inorganic filler (b2) having an average primary particle size of 230 nm to 1,000 nm, 90% or more of the number of individual particles constituting the spherical inorganic filler (b2) are present in a range of 5% greater or less than the average primary particle size, the following formula (1) is satisfied:

$$nP < nF_{b2} \quad (1)$$

wherein nP represents the refractive index of a polymer of the polymerizable monomer (A) at 25° C.; and $nF_{b2}$ represents the refractive index of the spherical inorganic filler (b2) at 25° C., and
the maximum point of the reflectance obtainable at the time of measuring the spectral reflectance of a cured product having a thickness of 1 mm of the curable composition using a color difference meter on a black background has a wavelength of 550 nm to 770 nm.

10. A dental curable composition consisting of the curable composition according to claim 1.

11. A dental filling restorative material consisting of the dental curable composition according to claim 10.

12. A dental curable composition consisting of the curable composition according to claim 9.

13. A dental filling restorative material consisting of the dental curable composition according to claim 12.

* * * * *